US011857685B2

(12) United States Patent
Leppert et al.

(10) Patent No.: US 11,857,685 B2
(45) Date of Patent: Jan. 2, 2024

(54) TREATMENT METHOD AND PRODUCT FOR UTERINE FIBROIDS USING PURIFIED COLLAGENASE

(71) Applicants: BioSpecifics Technologies LLC, Malvern, PA (US); Duke University, Durham, NC (US)

(72) Inventors: Phyllis Carolyn Leppert, Salt Lake City, UT (US); Thomas L. Wegman, N. Merrick, NY (US)

(73) Assignees: BioSpecifics Technologies LLC, Malvern, PA (US); Duke University, Durham, NC (US)

( * ) Notice: Subject to any disclaimer, the term of this patent is extended or adjusted under 35 U.S.C. 154(b) by 304 days.

(21) Appl. No.: 17/222,222

(22) Filed: Apr. 5, 2021

(65) Prior Publication Data
US 2021/0220284 A1   Jul. 22, 2021

Related U.S. Application Data

(63) Continuation of application No. 16/506,435, filed on Jul. 9, 2019, now abandoned, which is a continuation of application No. 14/213,957, filed on Mar. 14, 2014, now Pat. No. 10,369,110.

(60) Provisional application No. 61/790,070, filed on Mar. 15, 2013.

(51) Int. Cl.
| A61K 9/48 | (2006.01) |
| A61K 38/48 | (2006.01) |
| A61K 45/06 | (2006.01) |
| A61K 9/107 | (2006.01) |
| A61K 38/43 | (2006.01) |
| A61K 9/00 | (2006.01) |

(52) U.S. Cl.
CPC .............. *A61K 9/48* (2013.01); *A61K 9/0019* (2013.01); *A61K 9/0034* (2013.01); *A61K 9/1075* (2013.01); *A61K 38/43* (2013.01); *A61K 38/4886* (2013.01); *A61K 45/06* (2013.01); *C12Y 304/24003* (2013.01)

(58) Field of Classification Search
None
See application file for complete search history.

(56) References Cited

U.S. PATENT DOCUMENTS

| 3,821,364 A | 6/1974 | Chiulli et al. |
| 4,524,065 A | 6/1985 | Pinnell |
| 5,252,481 A | 10/1993 | Holjevac et al. |
| 5,256,140 A | 10/1993 | Fallick |
| 5,589,171 A | 12/1996 | Wegman |
| 5,830,741 A | 11/1998 | Dwulet et al. |
| 6,086,872 A | 7/2000 | Wegman |
| 7,811,560 B2 | 10/2010 | Sabatino |
| 2003/0022856 A1 | 1/2003 | Richardson et al. |
| 2003/0026844 A1 | 2/2003 | Lee et al. |
| 2005/0227910 A1 | 10/2005 | Yang et al. |
| 2006/0251581 A1* | 11/2006 | McIntyre ........... A61K 49/0002 424/9.4 |
| 2007/0003541 A1 | 1/2007 | Faudoa |
| 2007/0224183 A1* | 9/2007 | Sabatino ............ A61K 38/4886 424/94.63 |
| 2009/0053276 A1 | 2/2009 | Richard |
| 2010/0021416 A1 | 1/2010 | Lichter et al. |
| 2010/0035868 A1 | 2/2010 | Jabbour |
| 2010/0086971 A1 | 4/2010 | Suppmann et al. |
| 2012/0315265 A1 | 12/2012 | Lai et al. |
| 2013/0129663 A1 | 5/2013 | Friberg et al. |
| 2013/0195828 A1 | 8/2013 | Kibbe et al. |
| 2013/0217789 A1 | 8/2013 | Taylor et al. |
| 2013/0287759 A1 | 10/2013 | Munoz Montano |
| 2014/0271612 A1 | 9/2014 | Leppert et al. |

FOREIGN PATENT DOCUMENTS

| AU | 2012200863 A1 | 3/2012 | |
| CA | 2 308 842 A1 | 12/2000 | |
| CA | 2 643 171 A1 | 9/2007 | |
| EP | 0468411 A2 | 1/1992 | |
| EP | 2130551 B1 | 9/2009 | |
| EP | 2133415 A1 | 12/2009 | |
| GB | 2323530 A * | 9/1998 | ......... A61K 38/4886 |
| JP | 2002530873 A | 9/2002 | |
| JP | 2011528716 A | 11/2011 | |
| RU | 2180002 C2 | 2/2002 | |
| WO | 0030182 A2 | 5/2000 | |
| WO | 2006121968 A2 | 11/2006 | |
| WO | 2007089851 A2 | 8/2007 | |
| WO | 2007/100675 A3 | 9/2007 | |
| WO | 2010011605 A2 | 1/2010 | |
| WO | 2011/130537 A2 | 10/2011 | |

(Continued)

OTHER PUBLICATIONS

Jayes, F.L. et al. Oct. 24, 2012. Treatment of uterine fibroids with highly purified clostridial collagenase. American Society for Reproductive Medicine (ASRM) Abstracts. P-405. p. S232.*

Taylor, D.K. et al. 2012 Spring. Treatment for uterine fibroids: searching for effective drug therapies. Drug Discovery Today: Therapeutic Strategies 9(1): e41-e49; specif. pp. e41, e46, e47.*

Thomas, A. et al. 2010. The emerging role of Clostridium histolyticum collagenase in the treatment of Dupuytren disease. Therapeutics and Clinical Risk Management 6: 557-572; specif. pp. 557, 560, 561, 562, 565, 566, 567.*

Leppert, P.C. et al. 2006. A new hypothesis about the origin of uterine fibroids based on gene expression profiling with microarrays. American Journal of Obstetrics and Gynecology 195: 414-420; specif. pp. 415, 416.*

(Continued)

*Primary Examiner* — Michael Barker
*Assistant Examiner* — Sharon M. Papciak
(74) *Attorney, Agent, or Firm* — BakerHostetler

(57) ABSTRACT

Compositions and methods for treating uterine fibroids are described, wherein a uterine fibroid treatment agent comprising collagenase in an amount effective to cause shrinkage of uterine fibroids is injected or inserted into the uterine fibroid.

11 Claims, 17 Drawing Sheets

(10 of 17 Drawing Sheet(s) Filed in Color)

(56) References Cited

FOREIGN PATENT DOCUMENTS

| WO | 2012/031245 A1 | 3/2012 |
|----|----------------|--------|
| WO | 2012041512 A1 | 4/2012 |
| WO | 2013059619 A1 | 4/2013 |
| WO | 2014144859 A1 | 9/2014 |
| WO | 2015/108901 A1 | 7/2015 |

OTHER PUBLICATIONS

Dictionary of Chemical Engineering. Viscosity. Oxford University Press (publisher). First edition. Copyright 2014. Oxford University Press. Ed.: Carl Schaschke. Editorial Offices, Oxford, UK. p. 403.

Kikuchi, T. et al. 1998. Instr-articular injection of collagenase induces experimental osteoarthritis in mature rabbits. Osteoarthritis and Cartilage 6:177-186. Specif. pp. 177, 178.

Brandhorst, H. et al. 2008. The ratio between collagenase class I and class II influences the efficient islet release from the rat pancreas. Transplantation 85: 456-46. specif. pp. 456, 457.

Reconsideration Report by Examiner before Appeal issued for Japanese application No. 2016-503099 dated Aug. 20, 2019, 7 pages.

Reconsideration Report by Examiner before Appeal issued for Japanese application No. 2015-245310 dated Aug. 20, 2019, 5 pages.

Gilpin, D., et al., "Injectable collagenase clostridium histolyticum: A new nonsurgical treatment for Dupuytren's disease," J Hand Surg Am 2010, 35(12):2027-38, doi:10.1016/j.jhsa.2010.08.007.

Wahashi, M., et al., "Immunohistochemical analysis of collagen expression in uterine leiomyomata during the menstrual cycle," Experimental and Therapeutic Medicine 2011, 2:287-290.

Pharmaceuticals and Medical Devices Agency (PMDA) website, Jun. 2015, http://www.info.pmda.go.jp/downfiles/ph/PDF/100898_2900401D1020_1_01.pdf, 2 pages.

Dhaneshwar, S., et al., "Dextran: A promising macromolecular drug carrier," Indian Journal of Pharmaceutical Sciences, Nov.-Dec. 2006, 705-714.

Xiaflex, https://www.rxlist.com/xiaflex-drug.htm#description, Jul. 13, 2018, 3 pages.

Office Action issued in Japanese patent apln. 2016-503099 dated Mar. 18, 2020, with English translation, 24 pages.

Office Action issued in Japanese patent apln. 2015-245310 dated Mar. 24, 2020, with English translation, 45 pages.

Australian Examination Report No. 1 for AU 2015206597 dated May 23, 2019, 6 pages.

Office Action in JP application No. 2019-072161 with English translation dated May 12, 2020, 17 pages.

Examination Report No. 2 for Australian application No. 2019219834 dated Mar. 10, 2022, 4 pages.

Examination report No. 1 for Australian patent application No. 2016322911 dated May 3, 2021, 6 pages.

Examination report No. 1 for Australian patent application No. 2019219834 dated Mar. 22, 2021, 5 pages.

European Search Report for EP 20201646.5 dated Apr. 30, 2021, 9 pages.

Jeong, B. et al., 2000, "Thermogelling biodegradable polymers with hydrophillic backbones: PEG-g-PLGA." Macromolecules 33:8317-8322. specfic. p. 8317, 8320.

Stewart, E. A., Jan. 27, 2001, "Uterine fibroids." The Lancet 357:293-298, specif. p. 293.

Taylor, D. K., et al., 2011. "Temperature-responsive biocompatible copolymers incorporating hyperbranched polyglycerols for adjustable functionality." Journal of Functional Biomaterials 2:173-194, specif. pp. 173, 174.

Thomas, A. et al. 2010. The emerging role of Clostridium histolyticum collagenase in the treatment of Dupuytren disease. Therapeutics and Clinical Risk Management 6: 557-572. specif. pp. 557, 560, 561, 562, 565.

Examination Report in Canadian patent application No. 2907255 dated Sep. 3, 2019, 6 pages.

Office Action issued in U.S. Appl. No. 14/853,245 dated Jun. 15, 2017, 29 pages.

International Search Report and Written Opinion issued in PCT/US2016/051670 dated Nov. 21, 2016, 12 pages.

Canadian Office Action issued in CA 2,907,255 dated Feb. 23, 2017, 7 pages.

Taylor, D., et al., "Putting the Moose on the Table: Understanding the Molecular Biology of Uterine Fibroids and Development of Non-invasion Treatment," XP055257658, 64 pages, Oct. 28, 2012.

Taylor, D., et al., "Treatment for Uterine Fibroids: Searching for Effective Drug Therapies," Drug Discovery Today Therapeutic Strategies, vol. 9, No. 1, pp. e41-e49, 2012.

Jayes, F. L., et al., "Treatment of Uterine Fibroids with Highly Purified Clostridal Collagenase," Fertility and Sterility, vol. 98, No. 3, p. S232, XP055127058, Oct. 24, 2012.

Taylor, D., et al., "Recent scientific advances in leiomyoma (uterine fibroids) research facilitates better understanding and management," F1000Research, XP055257667, 11 pages, Jul. 6, 2015.

Extended European Search Report, issued in EP 16150076.4 dated Mar. 31, 2016, 11 pages.

Canadian First Examination Report issued in CA 2,907,255 dated Dec. 23, 2015, 7 pages.

Bonnerjea, J., et al., "Protein purification: the right step at the right time," Biotechnology, V. 4, 1986, pp. 954, 956 and 958.

Kågedal, L., et al., "Chemical, physical, and chromatographic properties of Superdex 75 prep grade and Superdex 200 prep grade gel filtration media," J. of Chromatography A, V. 537, 1991, pp. 17-32.

Office Action issued in Canadian application No. 2,643,171, dated Mar. 1, 2012, 3 pages.

International Search Report and Written Opinion in corresponding application No. PCT/US2012/029492, dated Aug. 20, 2012, 19 pages.

International Search Report and Written Opinion in corresponding application No. PCT/US2014/029448, dated Jul. 23, 2014, 10 pages.

Jayes, F. L., et al., "Treatment of uterine fibroids with highly purified clostridial collagenase," ASRM Abstracts, vol. 98, No. 3, Supplement, Sep. 2012, 1 page.

Notice of Acceptance for Australian patent application No. 2015261743 dated Aug. 21, 2017, 3 pages.

Office Action in Japanese application No. 2016-503099 dated Jan. 5, 2018, 7 pages.

Office Action in Japanese application No. 2015-245310 dated Jan. 19, 2018, 13 pages.

Office Action in Japanese application No. 2016-503099 dated Dec. 7, 2018, 8 pages.

Office Action in Japanese application No. 2015-245310 dated Dec. 4, 2018, 9 pages.

Behera, MD, M.A., et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences, vol. 14, No. 8S, pp. 63-76 (Dec. 2007).

Brunengraber, MD, L.N. et al., "Injectable Clostridium Histolyticum Collagenase as a Potential Treatment for Uterine Fibroids," Reproductive Sciences, vol. 21(12), pp. 1452-1459 (2014).

Soledad, MD, J., et al., "Mechanical Signaling in Reproductive Tissues: Mechanisms and Importance," Reproductive Sciences, vol. 21(9). pp. 1093-1107 (2014).

Leppert, P.C., et al., "The Extracellular Matrix Contributes to Mechanotransduction in Uterine Fibroids," Hindawi Publishing Corporation, vol. 2014, Article ID 783289, pp. 1-12 (Jul. 3, 2014).

Norian, J.M., et al., "Characterization of tissue biomechanics and mechanical signaling in uterine leiomyoma," Matrix Biol., 31(1): 57-65, 12 pages. (Jan. 9, 2011).

Peavey, MD, M., et al., "Collagen-Binding α II Integrin Expression in Human Myometrium and Fibroids Utilizing a Novel RNA In Situ Probe," Reproductive Sciences vol. 21(9) pp. 1139-1144, (2014).

Rogers, BS, R., et al., "Mechanical homeostasis is altered in uterine leiomyoma," Am. J. Obstet. Gynecol., 198(4): 474.e1-474.11, 22 pages (Apr. 2008).

(56) References Cited

OTHER PUBLICATIONS

Thorne, J.T., et al., "Dynamic Reciprocity Between Cells and Their Microenvironment in Reproduction," Biology of Reproduction, 92(1), Article 25, pp. 1-10, online before print Nov. 19, 2014. DOI 10.1095/biorepord.114.121368.

Jayes, DVM, PhD, F.L., et al., "Loss of stiffness in collagen-rich uterine fibroids after digestion with purified collagenase Clostridium histolyticum," American Journal of Obstetrics & Gynecology, 1.e1, 8 pages (2016).

Leppert MD, PhD, P.C. et al., "Comparative ultrastructure of collagen fibrils in uterine leiomyomas and normal myometrium," Fertil Steril, 82(3), pp. 1182-1187 (Oct. 2004).

Non-Final Office Action dated Jun. 27, 2018, in U.S. Appl. No. 15/112,007, 12 pages.

Cuggino, J. C., et al., "Synthesis, charaterization and slow drug delivery of hydrogels based in N-acryloyl-tris-(hydroxymethyl) aminomethane and N-isopropyl acrylamide," Reactive & Functional Polymers, vol. 71, 2011, pp. 440-446.

Gill, H. S., & Prausnitz, M. R., "Does needle size matter?," Journal of Diabetes Science and Technology, vol. 1 (5), Sep. 2007, pp. 725-729.

Madan, M., et al., "In situ forming polymeric drug delivery systems," Indian Journal of Pharmaceutical Sciences, vol. 71(3), May-Jun. 2009, pp. 242-251.

Nguyen, M. K., & Lee D. S., "Injectable biodegradable hydrogels," Macromol. Biosci., vol. 10, 2010, pp. 563-579.

Examination Report dated Jun. 8, 2018, in Canadian application No. 2,907,255, 5 pages.

PCT International Search Report, issued in PCT/US2015/011296 dated Jun. 11, 2015, 3 pages.

Australian First Examination Report issued in AU 2015261743 dated Aug. 22, 2016, 4 pages.

Office Action issued in U.S. Appl. No. 15/112,007 dated Oct. 31, 2017, 51 pages.

Japanese Office Action issued in JP 2016 547001 dated Sep. 20, 2018, with English translation, 7 pages.

Examination Report No. 1 in Australian application No. 2014228477 dated May 22, 2018, 3 pages.

Communication from European Patent Office in application serial No. EP 16770624.1 dated Apr. 20, 2018, 3 pages.

International Preliminary Report dated Mar. 20, 2018, for corresponding application PCT/US2016/051670, 8 pages.

First Examination Report in European application No. 14721664.2 dated Jan. 15, 2018, 5 pages.

First Examination Report in European application No. 16150076.4 dated Jan. 12, 2018, 6 pages.

* cited by examiner

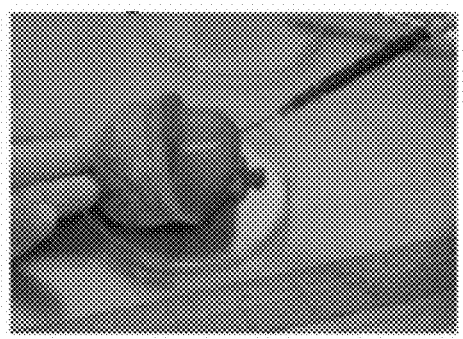
Fig. 4A                    Fig. 4B

Fig. 6A 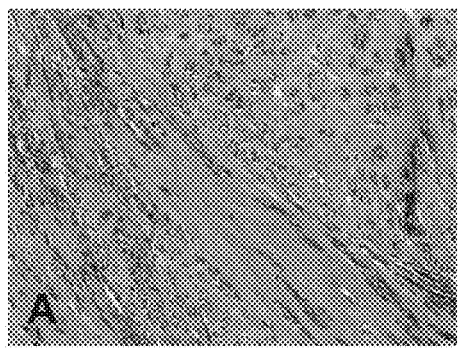 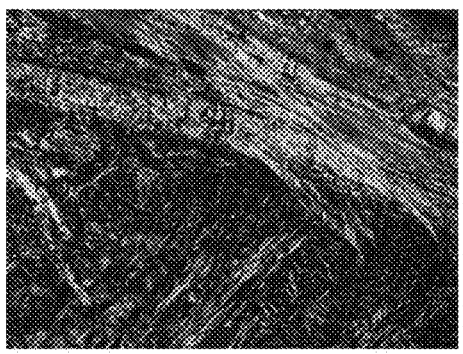 Fig. 6B
Fig. 6C 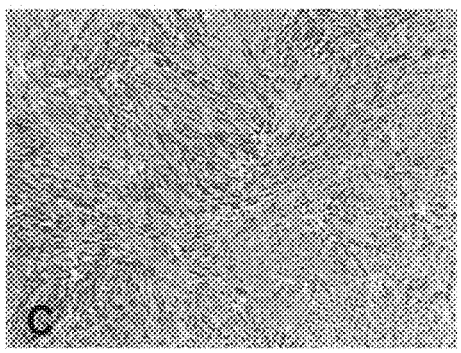 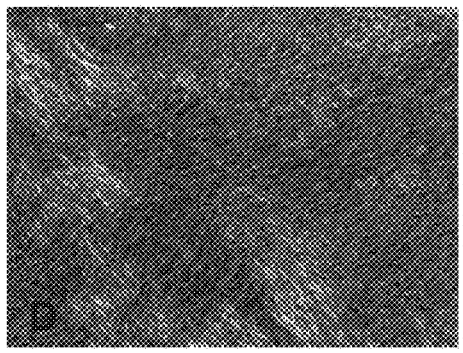 Fig. 6D

TREATMENT METHOD AND PRODUCT FOR UTERINE FIBROIDS USING PURIFIED COLLAGENASE

CROSS-REFERENCE TO RELATED APPLICATIONS

This application is a continuation of U.S. application Ser. No. 16/506,435, filed on Jul. 9, 2019, which is a continuation of U.S. application Ser. No. 14/213,957, filed on Mar. 14, 2014, now U.S. patent Ser. No. 10/369,110, which claims priority to U.S. Provisional Application Ser. No. 61/790,070, filed on Mar. 15, 2013, which are hereby incorporated by reference in their entireties.

FIELD OF THE INVENTION

The present invention relates to methods and products for medical treatment designed to reduce, shrink change the viscoelastic properties of, soften or eliminate unwanted tissue such as uterine fibroid tissue.

BACKGROUND OF THE INVENTION

Uterine fibroid tumors (also referred to as "uterine fibroids" or "leiomyomas") are non-cancerous tumors of the uterine wall that occur in 20 to 50% of women, and have an astonishingly high accumulative incidence. Current studies demonstrate that by age 50, 70-80% of women have developed uterine fibroids, with higher incidence in African-American women, who commonly develop fibroids earlier than other racial groups. A significant number of those with uterine fibroids suffer from debilitating pelvic pain, heavy and prolonged bleeding (which may lead to anemia and iron deficiency), bowel and bladder dysfunction and infertility. Uterine fibroids also cause symptoms such as low back pain, urinary frequency and urgency, pain during intercourse (dyspareunia), and negative impact on fertility. They are associated with high morbidity from uterine bleeding and pain along with health care costs estimated to be between $2.1 and $34.4 billion annually in the United States alone. Therefore, uterine fibroids have a significant impact on the health and well-being of reproductive age women and on the economy. After menopause, generally, fibroids shrink and only rarely cause problematic symptoms.

The etiology of this disease remains unknown, therefore there are no methods of preventing uterine fibroids. Several treatments are available, but hysterectomy is the only treatment which can permanently eliminate fibroids. The majority of the hysterectomies performed in the United States each year are due to uterine fibroids. It is obvious, but rarely stated in the literature, that hysterectomies lead to irrevocable loss of fertility. This invasive surgery also has a high cost, financially, socially and otherwise. It is associated with lengthy recovery times, potential for sometimes severe post-operative complications, and physical discomfort. Thus, this solution is far from ideal.

Other surgical methods such as myomectomy (surgical removal of the fibroid tissue leaving the remainder of the uterus intact) is commonly used, but may not be suitable in cases where the fibroids are too large or too numerous to leave enough normal tissue behind. Further, the fibroids often recur. In addition, about three-quarters of myomectomy surgeries are open surgeries involving an abdominal incision. Therefore, this method also is associated with complications, discomfort, long recovery, and potentially loss of fertility as well. Myolysis and cryomyolysis, in which uterine fibroids are burned or frozen via laparoscopic surgery, can be used to cause the fibroids to shrink and die over time. However, multiple punctures of the fibroids are needed to treat the entire tumor, and the treatment may cause adhesions post-surgery. MRI guided focused ultrasound also is used in the treatment of uterine fibroids, but this procedure is very expensive, and does not permanently eliminate the fibroids. Uterine artery embolization, during which a catheter is inserted into a femoral artery and guided to a uterine fibroid artery for injection of small particles into the fibroid artery, blocks the supply of blood, resulting in death of the fibroid tissue. Although this procedure is less invasive than traditional surgery, post-surgical pain is a frequent problem. In addition, this therapy, like hysterectomy, is considered a standard treatment for women with no desire for future fertility. Alternatively, MRgFUS provides noninvasive fibroid-specific therapy utilizing high-intensity ultrasonography through the abdominal wall to cause coagulative necrosis in specific fibroids. Guidance and thermal monitoring is provided by dynamic real-time magnetic resonance imaging. The surgical procedures to destroy uterine fibroids while preserving the uterus also have major drawbacks and often are not completely successful, due to re-growth of the fibroid tumors.

Non-surgical, pharmaceutical-based medical therapies are available. Fibroids often are treated by medications aimed at treating the symptoms rather than the fibroid tumors themselves. In the early stages, physicians employ a "wait-and-see" approach, with no treatment or symptomatic treatment until the condition impacts the ability of the patient to function in normal life. Most fibroids are not treated unless they are causing symptoms. However, even in the absence of hysterectomy, fibroids, particularly subserosal fibroids, also can lead to infertility.

The pharmacotherapies which are aimed at shrinking fibroid tumors or preventing increase in size have been disappointing and often have significant side effects. Drugs have been studied and sometimes are effective at shrinking uterine fibroids, but many of these non-surgical therapies have been associated with systemic side effects and therefore have not been approved for clinical use. For example, selective progesterone receptor modulators (SPRM) have not been approved by the FDA due to their effects on the endometrium. Only one drug has been approved for use to shrink uterine fibroids: leuprolide acetate. This drug is used as a short-term treatment which suppresses ovarian function (and therefore causes significant menopausal side effects), shrinking fibroids prior to surgery. Other medical therapies have been suggested in the recent past such as selective estrogen receptor modulators (SERM), but clinical trial results have been disappointing.

Current treatment options for uterine fibroids are inadequate. Hence, there is a continuing need in the art for alternative therapies for the treatment of uterine fibroids which are not open procedures and which preserve the patient's uterus. In particular, because treatment of uterine fibroids costs billions of health care dollars each year, and yet this condition remains a significant problem, there is a need for treatment methods that reduce or eliminate symptoms, provide relief without highly invasive procedures, and which preserve fertility.

SUMMARY OF THE INVENTION

The following brief summary is not intended to include all features and aspects of the present invention, nor does it imply that the invention must include all features and aspects discussed in this summary.

Embodiments of the invention are designed to provide the advantage of formulations, compositions and methods for treatment of uterine fibroids which do not require open surgical procedures and which preserve the patient's uterus. Another advantage of the present invention is that injectable or insertable formulations are provided, which display improved retention of agents within uterine fibroid tissue, thereby improving delivery efficiency, while at the same time minimizing adverse effects such as nonspecific damage and systemic effects. These formulations, compositions and methods include injectable, implantable or insertable formulations which contain one or more uterine fibroid treatment agents, preferably at least a purified collagenase in an amount effective to shrink or eliminate fibroids that are exposed to the formulation.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

The application file contains at least one drawing executed in color. Copies of any patent or patent application publication from this application containing color drawing(s) will be provided by the Office upon request and payment of the necessary fee.

FIGS. 4A and 4B are photographs of an excised uterus, showing a uterine fibroid (FIG. 4A) and a uterine fibroid undergoing injection (FIG. 4B).

FIGS. 6A and 6B are micrographs that show control tissue. FIGS. 6C and 6D are micrographs that show tissue that has been degraded with collagenase.

FIG. 12A shows total collagen under non-reducing conditions. FIG. 12B shows total collagen under reducing conditions. FIG. 12C shows a sample depleted of type V collagen by selective salt precipitation. FIG. 12D shows a sample enriched in type V collagen by selective salt precipitation (Feng L, Leikin S et al. presented at XXIInd Meeting of the Federation of European Connective Tissue Societies (FECTS), Jul. 3-7, 2010).

FIG. 14A shows fibroid cells with phalloidin staining with magnification 40×. FIG. 14B shows phalloidin staining of a sections from a matched myometrial sample with magnification 40×. FIG. 14C shows fibroid specimen and magnification 21,000× and FIG. 14D shows a matched myometrium specimen at magnification 21,000×. Note the angular cell shape, reduced cytoplasm, and notched nucleus in the fibroid (C) compared with myometrium (D).

DETAILED DESCRIPTION OF THE INVENTION

Collagen is the major structural constituent of mammalian organisms and makes up a large portion of the total protein content of skin and other parts of the animal body. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. Some diseases and conditions are associated with excess collagen deposition and the erratic accumulation of fibrous tissue rich in collagen. Such diseases and conditions are collectively referred to herein as "collagen-mediated diseases".

It has now been found that uterine fibroids are a collagen-mediated disease, associated with excess collagen deposition and the erratic accumulation of fibrous tissue rich in collagen. The considerable variation in growth rates over time of individual fibroids, and microarray studies revealing that genes encoding for ECM proteins or related to ECM synthesis and secretion account for a large portion of changes in gene expression in fibroids compared with myometrium make dysregulation of ECM (extracellular matrix) a possible contributing factor to this condition.

Transforming growth factor (TGF) plays a role in fibroid development. Fibroids grow by deposition of altered collagen. The expression of other molecules is likewise altered in fibroids. For example, dermatopontin expression is decreased, fibronectin and glycosaminoglycans (GAG) are increased, alpha 11 integrin, a collagen-binding integrin is expressed. In addition, fibroids are resistant to apoptosis.

Figure 1A:
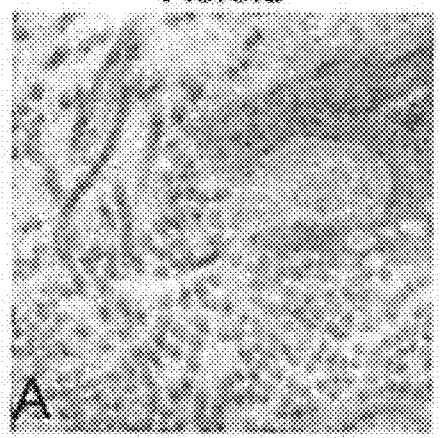
FIGS. 1A and 1B are electron micrographs (×31000) showing collagen fibrils in a uterine fibroid (1A) and in corresponding myometrium (1B).
Figure 1B:
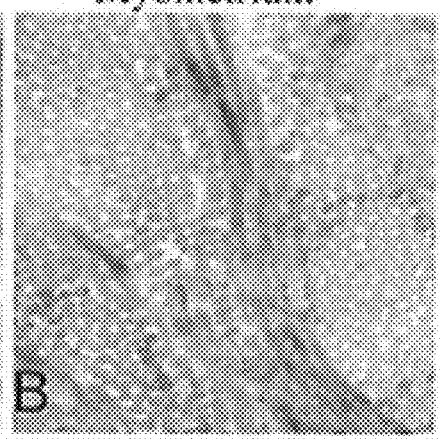

Recent studies indicate that fibroids are formed by the accumulation of extracellular matrix (ECM) as well as by cellular proliferation. See FIG. 1, noting the disordered collagen fibrils in the fibroid tissue. The appearance and spatial orientation of collagen fibrils in uterine fibroids were shorter, randomly aligned and widely dispersed compared with those of the myometrium. They were non-aligned and not parallel whereas in the adjacent myometrium the fibrils were well packed and parallel in orientation to each other, a finding that is characteristic of collagen containing tissue. Myofibroblast type cells (elongated appearance, notched nucleus) also have been found in uterine fibroids. The notched appearance of the fibroid cell nucleus represents folding and envaginations of the nuclear membrane due to cell contraction by stress fibers.

Figure 15:
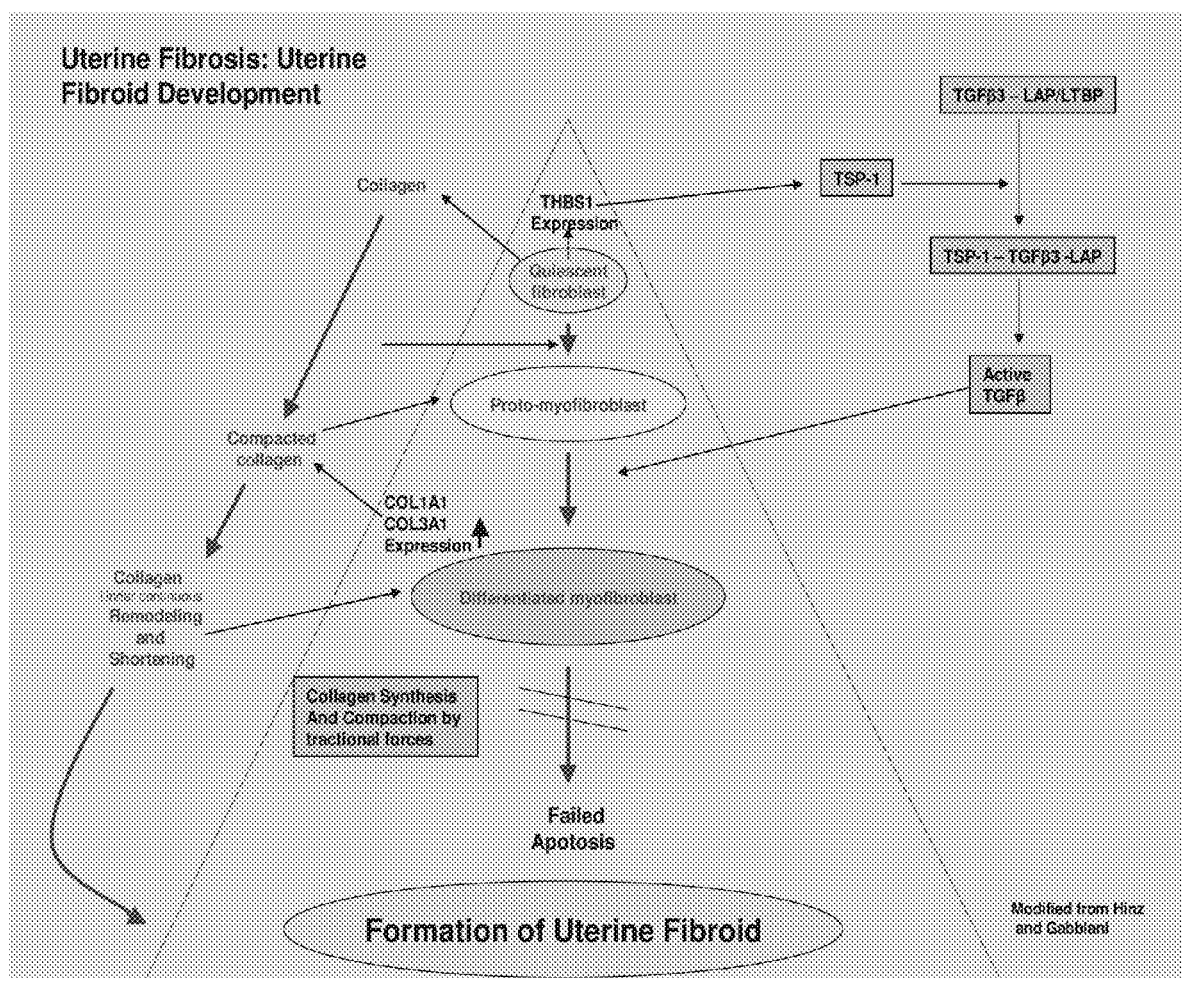
FIG. 15 is a schematic modified from FIG. 3 of Hinz and Gabbiani (Current Opinions in Biotechnology 2003, 14:38-46) that shows how TGF-β is a key mediator in fibrosis. TGF-β stimulates differentiation of fibroblasts into myfibroblasts, promotes the transcription of collagen, and stimulates extracellular matrix (ECM) accumulation. The schematic also shows the role of mechanotransduction and the role of the ECM in fibroid development. The ECM accumulation exerts compression on cells. The cells product increased ECM, which leads to mechanotransduction of increased collagen synthesis and deposition. Apoptosis of fibroid cells does not occur, and cells produce even more collagen.
Figure 16:
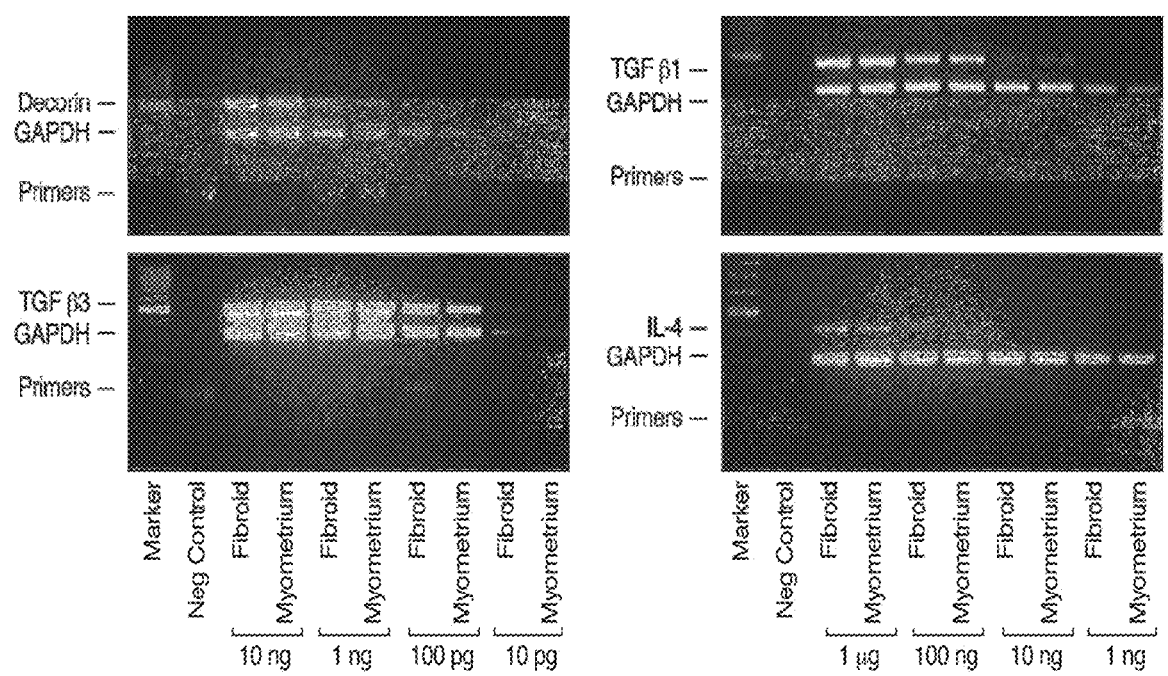
FIG. 16 is a set of representative gels of products from reverse transcriptase-PCR reactions for decorin, TGF-$β_1$, TGF-$β_3$ and interleukin-4. Paired leiomyoma (fibroid) and myometrium samples are as depicted. Leiomyoma-myometrium pairs are arranged in 10-fold dilutions of total RNA in each reaction. The negative control was a reaction containing primers but no RNA template. GAPDH was amplified as an internal control for assessment of amplification and similar amounts of RNA in samples. Lane markers are shown at the far left of the gel. (Catherino et al. (2004) Genes, Chromosomes & Cancer 40:204-217.)
Figure 17:
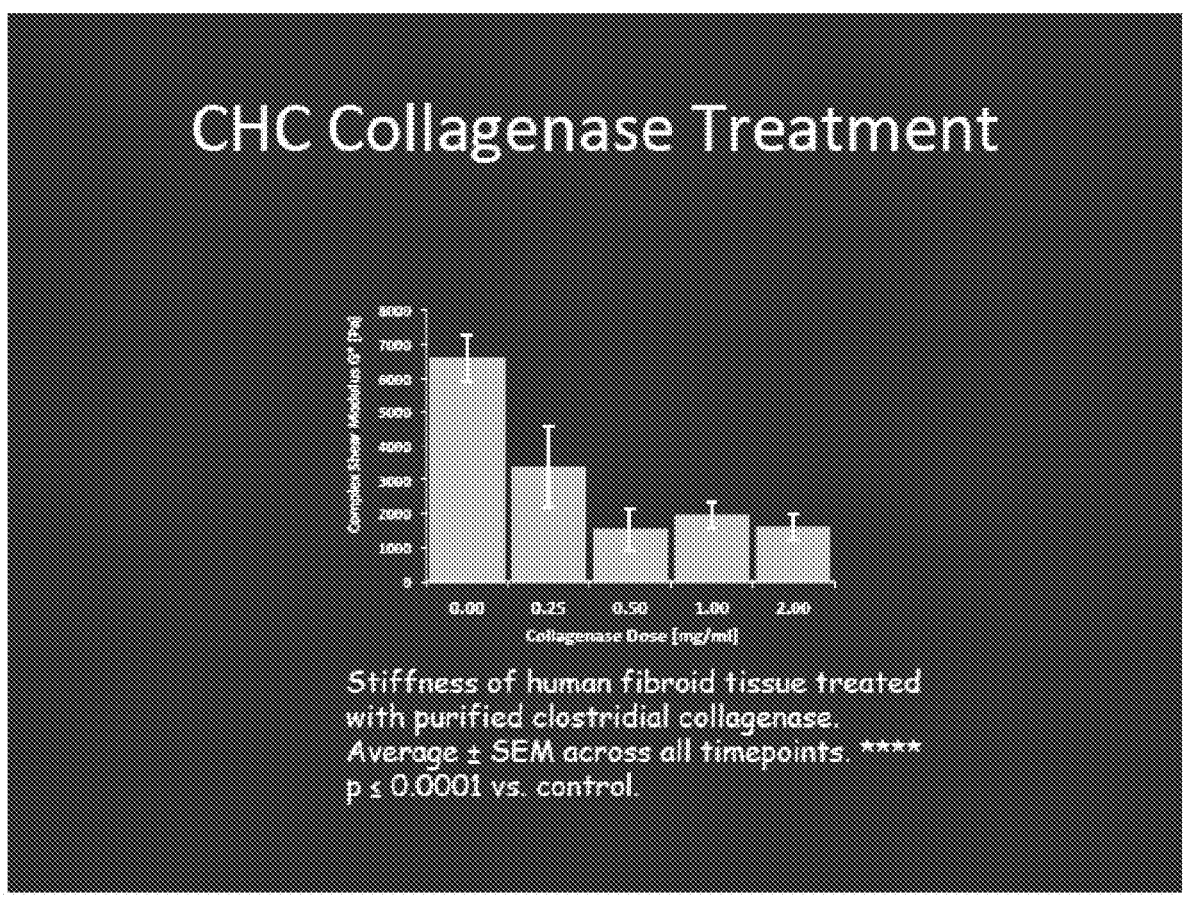
FIG. 17 shows the complex shear modulus (stiffness) of human fibroid tissue treated with purified clostridial collagenase.

Therefore, the present invention takes advantage of collagenase, an enzyme that has the specific ability to digest collagen, to treat uterine fibroids. Degradation of the collagen not only causes collagenolysis, it also reduces the increased cell compression leading to mechanotransduction. Thereby, the cycle of increased collagen secretion and enlargement of the uterine fibroid is broken. In summary, uterine fibroids contain an abundance of altered collagen consistent with fibrosis and stiffness. A stiff extracellular matrix (ECM) exerts force against individual cells. Mechanotransduction alters cell signaling and prevents apoptosis, and thus collagen accumulation continues. (See, FIG. 15.) Uterine fibroids grow at individual rates suggesting that mechanical transduction of tumors is responsible for variation in growth rates.

This specification describes embodiments of an invention for treatment to reduce the symptoms of uterine fibroids, shrink uterine fibroids, reduce the stiffness and mechanical stress of fibroid tissue on the uterus and/or eliminate uterine fibroids by local delivery of a purified collagenase composition to avoid systemic side-effects and harm to other tissues. In general, some of the preferred methods use a syringe and needle under ultrasound or other visualization for guided injection of purified collagenase directly into the uterine fibroid tissue to be treated. The collagenase product preferably is in a vehicle for delivery, such as a nanocarrier or other protective or sustained release carrier.

Because the center of fibroids is more fibrotic and contains smaller vascular capillary beds than the periphery, and due to a dense vascular capsule which surrounds the fibroid tumor, systemic therapy is not likely to provide therapeutic tissue levels of a drug in the fibroid center while leaving the likely possibility of systemic effects. Thus, pharmacotherapy has not been successful for uterine fibroids. The local injection of a treatment agent under imaging guidance allows for exact tissue placement of the drug and greatly reduces the chance of systemic effects.

Uterine fibroids are classified into several types, based on their location, including subserosal, intramural, submucosal, pedunculated submucosal, fibroid in statu nascendi, and fibroid of the broad ligament. Any and all of these uterine fibroids are contemplated for treatment using the invention.

Myometrial Hyperplasia is a condition which can mimic uterine fibroid symptoms and may be a precursor lesion of these tumors. It is structural variation with irregular zones of hypercellularity and increased nucleus/cell ratio, causing a bulging, firm, enlarged uterus. The condition often leads to hysterectomy. Deeper MMH has lower cellularity, and tends to have increased collagen. Therefore, this condition also may be treated using the methods and compositions of the invention.

The local treatment of uterine fibroids by injection of collagenase can be conducted in an office or clinic visit under ultrasound guidance with minimal chance for sequelae. This method can be used to treat small to moderate size fibroids or asymptomatic fibroids, which currently are not treated at all, allowing the clinician to prevent potentially debilitating symptoms and preservation of fertility in women of child-bearing years, and also larger fibroids, eliminating the need for hysterectomy for this disease. Thus, the methods of this invention are contemplated to be useful to treat any stage or type of uterine fibroid disease.

Collagenase for use according to the invention may be obtained from any convenient source, including mammalian (e.g., human, porcine), crustacean (e.g., crab, shrimp), fungal, and bacterial (e.g., from the fermentation of *Clostridium, Streptomyces, Pseudomonas, Vibrio* or *Achromobacter iophagus*). Collagenase can be isolated from a natural source or can be genetically engineered/recombinant. One common source of crude collagenase is from a bacterial fermentation process, specifically the fermentation of *Clostridium histolyticum*. The crude collagenase obtained from *C. histolyticum* can be purified using any of a number of techniques known in the art of protein purification, including chromatographic techniques. Collagenase compositions useful for the invention also can be prepared using any commercially available or isolated collagenase activity, or by mixing such activities. For example, purified collagenase can be provided by Biospecifics Technologies, Lynbrook, N.Y.

Preferred collagenases for use in the invention are from *C. histolyticum*, i.e., collagenase class I and class II. A practical advantage of using *C. histolyticum* for the production of collagenases is that it can be cultured in large quantities in simple liquid media, and it regularly produces amounts of proteolytic enzymes which are secreted into the culture medium. Bovine products have been used in culture media in the fermentation of *C. histolyticum*, but these run the risk of contamination by agents which cause transmissible spongiform encephalopathies (TSEs; e.g., prions associated with bovine spongiform encephalopathy or "mad cow disease"). Therefore, it is preferred to avoid such bovine products. An animal-product-free system is preferred. The H4 strain of *Clostridium histolyticum*, originally developed in 1956 can serve as a source for cells for culture. This strain, and a strain derived from the H4 strain, named the ABC *Clostridium*

*histolyticum* master cell bank (deposited as ATCC 21000) were developed using animal products, but are suitable to use in the invention.

U.S. Pat. No. 7,811,560, which is incorporated herein by reference in its entirety, discloses methods of producing collagenases. Using soybean derived fermentation medium, the methods described therein generated separately highly purified collagenase I and II. This patent also discloses methods of producing highly purified collagenases using culture media containing porcine-derived products. Any of these methods are suitable for use with the invention. U.S. Patent Publication 2010/0086971, which is also incorporated herein by reference in its entirety, discloses numerous fermentation recipes which are based on vegetable peptone, including soybean-derived peptone, or vegetable-derived peptone plus fish gelatin. The methods described in this publication are suitable to produce growth of *Clostridium* and collagenase activities. These methods also are suitable and contemplated for use with the invention, however any method known in the art of producing collagenase enzyme activity may be used.

In preferred culture methods, the peptone is from a plant source selected from the group consisting of soy bean, broad bean, pea, potato, and a mixture thereof. The peptone may be selected from the group consisting of Oxoid VG100 Vegetable peptone No. 1 from pea (VG100), Oxoid VG200 Vegetable peptone phosphate broth from Pea (VG200), Merck TSB CASO-Bouillion animal-free (TSB), Invitrogen Soy bean peptone No 110 papainic digest (SP6), Fluka Broad bean peptone (BP), Organotechnie Plant peptone E1 from potato (E1P), BBL Phytone™ peptone and BD Difco Select Phytone™.

In a preferred embodiment of the invention, a single type of peptone is present in the nutrient composition of the invention, whereby the peptone is selected from the group consisting of BP, E1P, Soy bean peptone E110, VG100, and VG200, and whereby the concentration of the peptone in the composition is about 5% weight by volume. In yet another very much preferred embodiment of the invention, a single type of peptone is present in the nutrient composition of the invention, whereby the peptone is BBL phytone peptone or Difco Select Phytone™ UF, and whereby the concentration of the peptone in the composition is about 10-13% weight by volume.

Preferred methods of isolating collagenase avoid undesirable contaminating proteases such as clostripain. Clostripain, a cysteine protease, is believed to be a major cause of collagenase degradation and instability, and is present in *Clostridium* culture. When such proteases are present in a crude collagenase mixture, one must take extra precautions to neutralize the proteases, including using protease inhibitors, such as leupeptin, and performing all of the purification steps in specially designed cold rooms with chilled solutions to reduce protease activity. Preferred methods of isolation therefore take advantage of one of two approaches to avoid clostripain: remove clostripain as early as possible in the purification method or reduce clostripain production during the fermentation stage.

Preferred collagenase compositions are produced by fermenting *C. histolyticum* in medium free of animal material-derived ingredients and are substantially free of clostripain, and thus are highly stable. "Substantially free" indicates that the collagenase contains less than 10 U clostripain per mg total collagenase, more preferably less than 5 U/mg, and most preferably about 1 U/mg or less, and/or that no visible band appears representing clostripain and/or degraded collagenase on SDS-PAGE gel compared to a reference standard.

Preferred methods for purifying collagenase involve using a "low glucose" medium as described herein, which contains less than about 5 g/L glucose, more preferably less than about 1 g/L, even more preferably less than about 0.5 g/L glucose, or is glucose-free, for culture of *C. histolyticum*. High salt concentrations in the growth media can reduce the amount of clostripain produced in culture, thus preferred media for *C. histolyticum* culture contain greater than about 5 g/L (or 0.5% w/v) total salt, more preferably greater than about 7.5 g/L (or 7.5%) total salt, and more preferably about 9 g/L (or 9%) or more. It is contemplated that any salt known to be suitable for use in microbiological fermentation media may be used in the current invention. In a preferred embodiment, chloride, phosphate or sulfate salts may be used. In a more preferred embodiment, the salts may be sodium chloride, potassium chloride, monosodium phosphate, disodium phosphate, tribasic sodium phosphate, potassium monophosphate, potassium diphosphate, tripotassium phosphate, calcium chloride, magnesium sulfate or various combinations thereof. In certain embodiments, potassium diphosphate may be about 0.1-0.3%, potassium phosphate may be about 0.75% to 0.175%, sodium phosphate may be about 0.2-0.5%, and/or sodium chloride may be about 0.15-0.35%. Preferably, the medium further comprises magnesium sulfate and vitamins, including, riboflavin, niacin, calcium pantothenate, pimelic acid, pyridoxine and thiamine.

In another preferred embodiment, the nutrient composition may contain 0.5-5% yeast extract, more preferably about 1-4%, and most preferably about 1.5-2.5%. Yeast extract is available from a variety of suppliers, including Cole Parmer (Vernon Hills, Ill.) and Fisher Scientific (Pittsburgh, Pa.).

In yet a preferred embodiment of the invention, the pH of the media is between pH 7 and pH 8. Even more preferred is a pH between about pH 7.2 and about pH 7.7, most preferably about 7.4.

The collagenase contemplated for use with the invention can be any collagenase which is active under the necessary conditions. However, preferred compositions contain a mass ratio of collagenase I and collagenase II which is modified or optimized to produce a desired or even a maximal synergistic effect. Preferably, collagenase I and collagenase II are purified separately from the crude collagenase mixture produced in culture, and the collagenase I and collagenase II are recombined in an optimized fixed mass ratio. Preferred embodiments contain a collagenase I to collagenase II mass ratio of about 0.5 to 1.5, more preferably 0.6 to 1.3, even more preferably 0.8 to 1.2, and most preferably, 1 to 1, however any combination or any single collagenase activity may be used.

A preferred method of producing collagenase which is contemplated for use with the invention involves fermenting *C. histolyticum* in a non-mammalian or non-animal medium, wherein the culture supernatant is substantially clostripain-free. The collagenases so produced can be isolated, purified, and combined to provide a composition for use in the invention which comprises a mixture of collagenase I and collagenase II in an optimized fixed mass ratio which is substantially clostripain-free. The crude collagenase obtained from fermentation of *C. histolyticum* may be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and/or metal chelation chromatography. Additionally, purification methods for collagenases are known, such as, for example, those described in U.S. Pat. No. 7,811,560, which is hereby incorporated by reference in its entirety.

Both collagenase I and collagenase II are metalloproteases and require tightly bound zinc and loosely bound calcium for their. Both collagenases have broad specificity toward all types of collagen. Collagenase I and Collagenase II digest collagen by hydrolyzing the triple-helical region of collagen under physiological conditions. Each collagenase shows different specificity (e.g. each have a different preferred target amino sequence for cleavage), and together they have synergistic activity toward collagen. Collagenase II has a higher activity towards all kinds of synthetic peptide substrates than collagenase I as reported for class II and class I collagenase in the literatures.

The preferred collagenase consists of two microbial collagenases, referred to as Collagenase ABC I and Collagenase ABC II. The terms "Collagenase I", "ABC I", and "collagenase ABC I" mean the same and can be used interchangeably. Similarly, the terms "Collagenase II", "ABC II", and "collagenase ABC II" refer to the same enzyme and can also be used interchangeably. These collagenases are secreted by bacterial cells. Preferably, they are isolated and purified from *Clostridium histolyticum* culture supernatant by chromatographic methods. Both collagenases are special proteases and share the same EC number (E.C 3.4.24.3). However, a collagenase or a combination of collagenases from other sources are contemplated for use with the invention. Collagenase ABC I has a single polypeptide chain consisting of approximately 1000 amino acids with a molecular weight of 115 kDa. Collagenase ABC II has also a single polypeptide chain consisting of about 1000 amino acids with a molecular weight of 110 kDa.

Collagenase acts by hydrolyzing the peptide bond between Gly-Pro-X, wherein X is often proline or hydroxyproline. Collagenase I acts at loci at ends of triple-helical domains, whereas Collagenase II cleaves internally. Hydrolysis continues over time until all bonds are cleaved.

Preferably, the collagenase product is at least 95% pure collagenase(s) and is substantially free of any contaminating proteases. More preferably, the collagenase product is 97% pure and most preferably 98% pure or more as determined by one or more of the following: sodium dodecyl sulfate polyacrylamide gel electrophoresis (SDS-PAGE); high performance liquid chromatography (HPLC); reverse-phase HPLC; or by enzymatic assays. The preferred collagenase product is essentially clostripain-free, and the purification preferably is performed in the absence of leupeptin. The preferred collagenase product for use with the invention has at least one specification selected from Table 1 below.

TABLE 1

Preferred Specifications for Collagenase Products

| Test | Specification | |
| --- | --- | --- |
| | ABC-I | ABC-II |
| Appearance | Clear colorless and essentially free from particulate matter | |
| Endotoxin | <10 EU/mL | |
| Identity (and purity) by SDS-PAGE (Reduced conditions, Coomasie) | Major collagenase band between 98-188 kDa ≥95% | Major collagenase band between 97-200 kDa ≥95% |

TABLE 1-continued

Preferred Specifications for Collagenase Products

| Test | Specification | |
| --- | --- | --- |
| | ABC-I | ABC-II |
| SRC assay (ABC-I) | 1967-3327 SRC units/mg | NA |
| GPA assay (ABC-II) | | NA81934-119522 GPA units/mg |
| Analysis of Proteins HPLC System (Aggregation by size exclusion chromatography) | ≥98% main peak; ≤2% aggregates by area | |
| Identity and purity by reverse phase liquid chromatography | Major peak (ABC I or ABC II), ≥95% by area; Retention times of ABC-I and ABC-II within 5% of reference | |
| Clostripain assay (BAEE assay) | ≤1 U/mg | |
| Bioburden | <1 cfu/mL | |

The collagenase products described for use herein are useful for the treatment of collagen-mediated disease, including uterine fibroids. Examples of other collagen mediated-diseases that may be treated by the compositions of the invention include but are not limited to: Dupuytren's disease; Peyronie's disease; frozen shoulder (adhesive capsulitis), keloids; tennis elbow (lateral epicondylitis); scarred tendon; glaucoma; herniated discs; adjunct to vitrectomy; hypertrophic scars; depressed scars such as those resulting from inflammatory acne; post-surgical adhesions; acne vulgaris; lipomas, and disfiguring conditions such as wrinkling, cellulite formation and neoplastic fibrosis.

In addition to its use in treating specific collagen-mediated diseases, the compositions of the invention also are useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. In general, the compositions of the present invention are useful for any application where the removal of cells or the modification of an extracellular matrix, are desired.

The collagenase compositions according this invention are designed to administer to a patient in need thereof a therapeutically effective amount of a collagenase composition as described, or a therapeutically effective amount of a pharmaceutical collagenase formulation as described. A "therapeutically effective amount" of a compound, composition or formulation is an amount of the compound which confers a therapeutic effect on the treated subject, at a reasonable benefit/risk ratio applicable to any medical treatment. A therapeutic effect includes but is not limited to a shrinkage or reduction in the size of one or more uterine fibroids (including elimination of the fibroid), liquification, partial liquification, or reduction in stiffness (increase in softness) or pressure in or around a uterine fibroid, a change in viscoelastic properties, or reduction in symptoms such as pain, hemorrhage and the like.

The therapeutic effect may be objective (i.e., measurable by some test or marker) or subjective (i.e., subject gives an indication of or feels an effect), and may be determined by the clinician or by the patient. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, and diet of the patient; the time of administration, route of administration, and rate of excretion of the specific compound employed; the duration of the treatment; drugs used in combination or contemporaneously with the specific compound employed; and like factors well known in the medical arts.

The term "patient" or "patient in need" encompasses any mammal having a uterus and uterine fibroids or symptoms thereof. Such "patients" or "patients in need" include humans or any mammal, including farm animals such as horses and pigs, companion animals such as dogs and cats, and experimental animals such as mice, rats and rabbits. Preferred patients are human females of child-bearing age.

The pharmaceutical compositions of this invention preferably are administered by injection, insertion or implantation directly into or onto the uterine fibroid tissue to be treated, i.e. local administration to the tissue to be treated. Other modes of administration contemplated included, but are not limited to transvaginal instillation or application onto the affected tissues, instillation or application during surgery (such as laparoscopy or hysteroscopy) onto the affected tissues, i.e. topical administration to the fibroid tissue, by spray or other application of a liquid, fluid or gel formulation.

Formulations of the present invention are injected/inserted into uterine tissue in a variety of forms, by a variety of routes, using a variety of apparatuses. In some embodiments, the formulation is injected/inserted using an apparatus consisting of a simple needle (e.g., a 10 gauge or smaller needle) and sample pusher (e.g., a mandrel or modified obturator). For example, according to one embodiment, a formulation (e.g., a rod-shaped or other shaped solid or semi-solid formulation, beads, suspension, gel, polymer or the like) is placed in the needle or in a syringe or other chamber affixed to the needle. Once the needle is placed at the desired depth and location in the tissue, the pusher is used to push the sample from the needle and into the tissue. In some embodiments, the sample pusher is provided with a holding clip or it is provided with a hollow end to secure the sample up to the time of delivery.

In still other embodiments, formulations in accordance with the present invention are injected/inserted via jet injection without a physical delivery channel such as a needle, as is known in the art. Typically, a compression system (e.g., a mechanical system or a gas, such as helium, nitrogen, carbon dioxide, etc.) is used to accelerate the formulations to a high enough velocity so that the formulation can penetrate the tissue to a desired depth. Jet injector devices can be, for example, disposable, or reusable with medication cartridges that are prefilled or non-prefilled medication cartridges. Examples of jet injectors include Biojector from Bioject, N.J., USA and the PowderJect® System from PowderJect, UK. In other embodiments, a device is employed that cores out a section of the fibroid (e.g., a biopsy device or tissue morcellator or laser radiation), thereby leaving behind a void for insertion of a dosage form.

The formulations for collagenase delivery to a patient generally are contemplated to comprise injectable or implantable formulations, or any fluid, liquid, solid, semi-solid, gel, or other composition which is suitable to administer the collagenase to the tissue to be treated as described herein. Formulations in accordance with the present invention may be formulated by any method known in the pharmaceutical arts. Thus, any injectable or implantable formulation known in the art and consistent with collagenase activity may be used. Formulations which create a depot or extended release of the active collagenase agent are contemplated. In particular, injectable extended or sustained release compositions are preferred, however any implantable formulation can be used. Such compositions produce or form a depot effect, where active agent is present in the tissue where administered and release active agent over a period of time to continuously treat the tissue. Immediate release injectable formulations, where the active agent is immediately released for activity upon administration, also are contemplated for use with the invention. These formulations are known in the art and can be adapted for use with the present invention by any person of skill.

In some embodiments, the injectable or insertable formulations of the present invention are solids, semi-solids or high-viscosity fluids. This improves dosage retention in the tissue, thereby improving delivery efficiency of the treatment agents and/or minimizing the adverse effects such as unintended, nonspecific tissue damage. "High viscosity" and other such terms are used herein to describe fluids having viscosities greater than 1000 centipoise as measured by any of a number of standard techniques, including, for example, a Brookfield Kinematic Viscometer, model HBDV-II+CP with a CPE-40 cone spindle, set at 37° C. and using a 0.5 rpm speed setting. "Low viscosity" fluids have viscosities less than this value.

In some embodiments, a formulation in accordance with the present invention is injected into a patient in a fluid state, whereupon it converts (or is converted) in vivo into a more readily retained form, for example, into a solid form (including conversion of an injected liquid into a solid, conversion of an injected semi-solid into a solid and conversion of a liquid into a gel), into a semi-solid form (including conversion of an injected liquid into a semi-solid, conversion of an injected semi-solid into a semi-solid having increased yield stress and/or viscosity and conversion of a liquid into a gel), or into a high-viscosity fluid (including conversion of a low-viscosity fluid into a high-viscosity fluid, and conversion of a high-viscosity fluid into a higher-viscosity fluid).

Preferred formulations for injection into a uterine fibroid use a carrier or nanocarrier. Appropriate carriers include solid or semi-solid pellets, beads or gel-forming polymers, high-viscosity liquids and the like to maintain the active collagenase in the tissue, protecting the active enzyme from action of the tissue or tissue components which could inactivate the collagenase, and allow steady release of the enzyme to the tissue for treatment. Any injectable dosage form which can protect and contain the active compound(s) in place may be used. In mammals, *C. histolyticum* collagenase is inhibited rapidly in the blood stream by serum. Therefore, systemic administration, or administration under conditions where the collagenase can be deactivated, or orally, where the collagenase can be degraded by digestive enzymes, is problematic.

Nanocarriers are designed to deliver and protect drug therapeutics (e.g. proteins, for example) from degradation. A nanocarrier formulation also is preferred because this method impedes diffusion and distribution of the drug away from the injected fibroid, prolongs release, delays inactivation, and therefore reduces the frequency of repeat injections. Any such nanocarrier known in the art can be used with the invention. Some of these nanocarriers also are referred to as thermoresponsive delivery systems.

Atrigel* comprises a water-insoluble biodegradable polymer (e.g., poly(lactic-co-glycolic acid, PLGA) dissolved in a bio-compatible, water-miscible organic solvent (e.g., N-methyl-2-pyrrolidone, NMP). In use, collagenase is added to form a solution or suspension. Both the PLGA molecular weight and lactide-glycolide molar ratio (L:G ratio) governs drug delivery. Using an L:G ratio of from 50:50 to 85:15 and a polymer concentration of from 34 to 50%, clinical studies have demonstrated a depot which was maintained for more than 3 months.

ReGel* is a 4000 Da triblock copolymer formed from PLGA and polyethylene glycol (PEG, 1000 Da or 1450 Da) in repetitions of PLGA-PEG-PLGA or PEG-PLGA-PEG. ReGel* is formulated as a 23 wt % copolymer solution in aqueous media. A drug is added to the solution and upon temperature elevation to 37° C. the whole system gels. Degradation of ReGel* to final products of lactic acid, glycolic acid and PEG occurs over 1-6 weeks depending on copolymer molar composition. Chemically distinct drugs like porcine growth hormone and glucagon-like peptide-1 (GLP-1) may be incorporated, one at a time, and released from ReGel*.

LiquoGel™ can work by mechanistically independent drug delivery routes: entrapment and covalent linkage. Two or more drugs can be delivered to the tumor site using this carrier. LiquoGel™ is a tetrameric copolymer of thermogelling N-isopropylacrylamide; biodegrading macromer of poly(lactic acid) and 2-hydroxyethyl methacrylate; hydrophilic acrylic acid (to maintain solubility of decomposition products); and multi-functional hyperbranched polyglycerol to covalently attach drugs. LiquoGel™ generally is formulated as a 16.9 wt % copolymer solution in aqueous media. The solution gels under physiological conditions and degrades to release drug contents within 1-6 days.

Any of the above carriers can be used as a nanocarrier with the invention. A preferred nanocarrier, however, contains hyperbranched polyglycerols (HPG), which have many desirable features. HPGs grow by imperfect generations of branched units and are produced in a convenient single step reaction. Previous problems of large polydispersities in molecular weight in their production have been overcome. The resulting polymers contain a large number of modifiable surface functional groups as well as internal cavities for drug interaction. Other polymer approaches cannot easily provide these properties without significant increases in the number of synthetic steps and, consequently, cost. HPG polymers are based on glycerol and because of structural similarity with polyethylene glycol, is biocompatible.

Additional components optionally can be added to the polymer, therefore, modified HPG polymers and co-polymers of HPG are contemplated. These additional components or monomers can include, for example, crosslinks, biodegradable moieties, and thermoresponsive moieties. For example, thermally responsive hydrogels are attractive for injection therapy since it is possible to inject the necessary fluid volume from a syringe maintained below body temperature and upon warming, the mechanical properties are increased, thereby restraining the material at the injection site. Poly(N-isopropylacrylamide) (poly-NIPAAm) is a thermally responsive polymer with a lower critical solution temperature (LCST) of approximately 32° C. Copolymers of HPG with NIPAAm are therefore contemplated for use with the invention, and are preferred. This nanocarrier has a versatile mesh size and can be customized to entrap small drug molecules, large proteins, or a mixture of components, and gels at body temperature to permit slow release as the nanocarrier biodegrades.

In preferred embodiments of the invention, formulations exist as a liquid at temperatures below body temperature and as a gel at body temperature. The temperature at which a transition from liquid to gel occurs is sometimes referred to as the LCST, and it can be a small temperature range as opposed to a specific temperature. Materials possessing an LCST are referred to as LCST materials. Typical LCST's for the practice of the present invention range, for example, from 10 to 37° C. As a result, a formulation injected below the LCST warms within the body to a temperature that is at or above the LCST, thereby undergoing a transition from a liquid to a gel.

Suitable LCST materials for use with the invention include polyoxyethylene-polyoxypropylene (PEO-PPO) block copolymers. Two acceptable compounds are Pluronic acid F127 and F108, which are PEO-PPO block copolymers with molecular weights of 12,600 and 14,600, respectively. Each of these compounds is available from BASF (Mount Olive, N.J.). Pluronic acid F108 at 20-28% concentration concentration, in phosphate buffered Saline (PBS) is an example of a suitable LCST material. One beneficial preparation is 22.5% Pluronic acid F108 in PBS. A preparation of 22% Pluronic acid F108 in PBS has an LCST of 37° C. Pluronic acid F127 at 20-35% concentration in PBS is another example of a suitable LCST material. A preparation of 20% Pluronic acid F127 in PBS has an LCST of 37° C. Typical molecular weights are between 5,000 and 25,000, and, for the two specific compounds identified above are 12,600 and 14,600. More generally, materials, including other PEO-PPO block copolymers, which are biodisintegrable, and which exist as a gel at body temperature and as a liquid below body temperature can also be used according to the present invention. Further information regarding LCST materials can be found in U.S. Pat. Nos. 6,565,530 B2 and 6,544,227 B2, each of which is hereby incorporated by reference.

Pharmaceutical formulations of the collagenase compounds for the invention include a collagenase composition formulated together with one or more pharmaceutically acceptable vehicles or excipients. As used herein, the term "pharmaceutically acceptable carrier or excipient" means a non-toxic, inert, solid, semi-solid or liquid filler, diluent, encapsulating material, vehicle, solvent, or formulation auxiliary of any type, and may be made available in individual dosage forms or in bulk. Other dosage forms designed to create a depot of the active compound also are contemplated for use with the invention. Dosage forms for collagenase suitable for use with the invention include, but are not limited to lyophilized or other dried powder for reconstitution prior to injection, in multiple or single dose amounts, individual dosage units ready for injection (which preferably also include one or more preservatives), frozen unit dosage forms, or any mode of preparation known in the art. The formulations also may be provided in the form of a kit, which can contain the collagenase in solid form, liquid or solvent for reconstitution and injection, and any equipment necessary for administration, such as a syringe and needle, particularly a specialized syringe and/or needle for administration to a uterine fibroid. Preferably, the dosage form has a largest dimension between 1 mm and 20 mm. Preferably, the formulations are sterile. The products may be sterilized by any method known in the art, such as by filtration through a bacterial-retaining filter or are produced under aseptic conditions. Other methods include exposing the formulation or components thereof to heat, radiation or ethylene oxide gas.

Some examples of materials which can serve as pharmaceutically acceptable carriers are solvents for injection as known in the art. Examples include, but are not limited to sterile water, buffering solutions, saline solutions such as normal saline or Ringer's solution, pyrogen-free water, ethyl alcohol, non-toxic oils, and the like, or any solvent compatible with injection or other forms of administration as described herein for use with the invention.

In addition, any solid excipients known in the art for use in pharmaceutical products can be used with the invention as a vehicle or filler, for example. Sugars such as lactose, glucose and sucrose; starches such as corn starch and potato starch; cellulose and its derivatives such as microcrystalline cellulose, sodium carboxymethyl cellulose, ethyl cellulose and cellulose acetate; powdered tragacanth; malt; gelatin; gums; talc; glycols such as propylene glycol; esters such as ethyl oleate and ethyl laurate; agar, and the like can be used. Buffering agents compatible with the active compounds and the methods of use are contemplated for use, including acid or alkali compounds, such as magnesium hydroxide and aluminum hydroxide, citric acid, phosphate or carbonate salts and the like. Non-toxic compatible excipients such as lubricants, emulsifiers, wetting agents, suspending agents, binders, disintegrants, preservatives or antibacterial agents, antioxidants, sustained release excipients, coating agents and the like (e.g., sodium lauryl sulfate and magnesium stearate) also may be used, as well as coloring agents, perfuming agents, viscosity enhancing agents, bioadhesives, and the like, according to the judgment of the formulator.

For example, one or more biodisintegrable binders may be included in the formulations of the present invention, typically in connection with dosage forms having solid characteristics. Where employed, a wide range of biodisintegrable binder concentrations may be utilized, with the amounts varying based, for example, on the desired physical characteristics of the resulting dosage form and on the characteristics of the uterine fibroid treatment agent that is selected (e.g., the degree of dilution, release delay, etc. that is desired/tolerated), among other considerations. The concentration of biodisintegrable binder typically ranges are from about 1 to 80 wt % of biodisintegrable binder, more typically about 5 to 50 wt %. A "biodisintegrable" material is one that, once placed in tissue such as uterine tissue, undergoes dissolution, degradation, resorption and/or other disintegration processes. Where such materials are included, formulations in accordance with the present invention will typically undergo at least a 10% reduction in weight after residing in tissue such as uterine tissue for a period of 7 days, more typically a 50-100% reduction in weight after residing in the tissue for a period of 4 days. Suitable biodisintegrable binders for use in connection with the present invention include, but are not limited to biodisintegrable organic compounds, such as glycerine, and biodisintegrable polymers, or any known disintegrant compound known in the art of pharmaceutics.

Where used, viscosity adjusting agent(s) are typically present in an amount effective to provide the formulation with the desired viscosity, for example, by rendering the formulation highly viscous, for example, in an amount effective to provide a viscosity between about 5,000 and 200,000 centipoise, more typically between about 10,000 and 100,000 centipoise, more typically between about 10,000 and 50,000 centipoise, and even more typically between about 20,000 and 40,000 centipoise. By providing formulations having viscosities within these ranges, the formulations can be injected into tissue, such as uterine tissue, using conventional injection equipment (e.g., syringes). However, due to their elevated viscosities, the formulations have improved retention within the tissue at the injection site. The concentration of the viscosity adjusting agent(s) that is (are) used can vary widely. Commonly, the overall concentration of the viscosity adjusting agent(s) is between about 1 and 20 wt %. In many embodiments, the viscosity adjusting agents are polymers, which may be of natural or synthetic origin and are typically biodisintegrable. The polymers are also typically water soluble and/or hydrophilic. However, in some embodiments, for instance where an organic solvent such as dimethylsulfoxide (DMSO) is used as a liquid component, the viscosity adjusting agent can be relatively hydrophobic. The polymeric viscosity adjusting agents include homopolymers, copolymers and polymer blends.

Examples of viscosity adjusting agents for the practice of the present invention include, but are not limited to the following: cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, hydroxyethyl starch (HES), dextran, dextran derivatives, chitosan, and alginic acid and its various salts, carrageenan, various gums, including xanthan gum, guar gum, gum arabic, gum karaya, gum ghatti, konjac and gum tragacanth, glycosaminoglycans and proteoglycans such as hyaluronic acid and its salts, heparin, heparin sulfate, dermatan sulfate, proteins such as gelatin, collagen, albumin, and fibrin, other polymers, for example, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide and poly (ethylene oxide-propylene oxide) (e.g., Pluronic acid), polyoxyethylene (polyethylene glycol), polyethyleneamine and polypyrridine, poly-metaphosphate (Kurrol salts), polyvinyl alcohol, additional salts and copolymers beyond those specifically set forth above, and blends of the foregoing (including mixtures of polymers containing the same monomers, but having different molecular weights), and so forth. Many of these species are also useful as binders.

In other embodiments of the invention, formulations or carriers are crosslinked, either prior to use or in vivo. Crosslinking is advantageous, for example, in that it acts to improve formulation retention (e.g., by providing a more rigid/viscous material and/or by rendering the polymer less soluble in a particular environment). Where the formulation is crosslinked in vivo, a crosslinking agent is commonly injected into tissue either before or after the injection or insertion of a formulation in accordance with the present invention. Depending on the nature of the formulation and the crosslinking agent, the formulation may be converted, for example, into a solid, into a semi-solid, or into a high-viscosity fluid.

Crosslinking agents suitable for use in the present invention include, any non-toxic crosslinking agent, including ionic and covalent crosslinking agents. For example, in some embodiments, polymers are included within the formulations of the present invention, which are ionically crosslinked, for instance, with polyvalent metal ions. Suitable crosslinking ions include polyvalent cations selected from the group consisting of calcium, magnesium, barium, strontium, boron, beryllium, aluminum, iron, copper, cobalt, lead and silver cations ions. Polyvalent anions include phosphate, citrate, borate, succinate, maleate, adipate and oxalate anions. More broadly, crosslinking anions are commonly derived from polybasic organic or inorganic acids. Ionic crosslinking may be carried out by methods known in the art, for example, by contacting ionically crosslinkable polymers with an aqueous solution containing dissolved ions.

In some embodiments, polymers are included, which are covalently crosslinkable, for example, using a polyfunctional crosslinking agent that is reactive with functional groups in the polymer structure. The polyfunctional crosslinking agent can be any compound having at least two functional groups that react with functional groups in the polymer. Various polymers described herein can be both covalently and ionically crosslinked.

Suitable polymers for ionic and/or covalent crosslinking can be selected, for example, from the non-limiting list of the following: polyacrylates; poly(acrylic acid); poly(methacrylic acid); polyacrylamides; poly(N-alkylacrylamides); polyalkylene oxides; poly(ethylene oxide); poly(propylene oxide); poly(vinyl alcohol); poly(vinyl aromatics); poly(vinylpyrrolidone); poly(ethylene imine); poly(ethylene amine); polyacrylonitrile; poly(vinyl sulfonic acid); polyamides; poly(L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; hydroxyethyl starch; chondroitin sulfate; guar; starch; and salts, copolymers, mixtures and derivatives thereof.

In one preferred embodiment, the collagenase is formulated as a lyophilized injectable composition formulated with lactose, sucrose or any suitable sugar. One preferred collagenase composition is a lyophilized injectable composition formulated with sucrose, Tris at a pH level of about 8.0. Most preferably, 1.0 mg of the drug substance of the invention is formulated in 60 mM sucrose, 10 mM Tris, at a pH of about 8.0 (e.g., about 20.5 mg/mL of sucrose and 1.21 mg/mL of Tris in the formulation buffer).

Preferred collagenase compositions for use in the invention comprise a mixture of collagenase I and collagenase II has a specific activity of at least about 700 SRC units/mg, such as at least about 1000 SRC units/mg, more preferably at least about 1500 SRC units/mg. One SRC unit will solubilize rat tail collagen into ninhydrin reaction material equivalent to 1 nanomole of leucine per minute, at 25° C., pH 7.4. Collagenase has been described in ABC units as well. This potency assay of collagenase is based on the digestion of undenatured collagen (from bovine tendon) at pH 7.2 and 37° C. for 20-24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute. One SRC unit equal approximate 6.3 ABC unit or 18.5 GPA unit. In one embodiment, each milligram of collagenase for injection will contain approximately 2800 SRC units.

Doses contemplated for administration by direct injection to the uterine fibroid tissue will vary depending on the size of the tissue to be treated and the discretion of the treating physician. However, doses generally are about 0.06 mg collagenase to about 1 mg collagenase per $cm^3$ of tissue to be treated or about 0.1 mg collagenase to about 0.8 mg collagenase per $cm^3$ of tissue to be treated, or about 0.2 mg collagenase to about 0.6 mg collagenase per $cm^3$ of tissue to be treated.

Formulations that contain an additional active agent or medication also are contemplated. Optional additional agents which can be included in the formulation for concomitant, simultaneous or separate administration include, for example, any pharmaceutical known in the art for shrinkage, treatment or elimination of uterine fibroids or their symptoms, or to assist in performance of the present treatment methods. For example, one or more fibroid treatment agents such as aromatase inhibitors (e.g., letrozole, anastrozole, and exemestande), progesterone receptor agonists and modulators (e.g., progesterone, progestins, mifepristone, levonoergestrel, norgestrel, asoprisnil, ulipristal and ulipristal acetate, telepristone), selective estrogen receptor modulators (SERMs) (e.g., benzopyran, benzothiophenes, chromane, indoles, naphtalenes, tri-phenylethylene compounds, arzoxifene, EM-652, CP 336,156, raloxifene, 4-hydroxytamoxifen and tamoxifen), gonadotrophin-releasing hormone analogs (GnRHa) (e.g., GnRH agonist peptides or analogs with D-amino acid alterations in position 6 and/or ethyl-amide substitutions for carboxyl-terminal Gly10-amide such as triptorelin or GnRH antagonists such as cetrorelix, ganirelix, degarelix and ozarelix), growth factor modulators (e.g., TGFb neutralizing antibodies), leuprolide acetate, non-steroidal anti-inflammatory drugs, inhibitors of the mTOR pathway, inhibitors of the WNT signaling pathway, vitamin D, vitamin D metabolites, vitamin D modulators, and/or an additional anti-fibrotic compound (e.g., pirfenidone and halofuginone) may be co-administered with collagenase in the same or a separate administration.

Chemical ablation agents also can be included in the formulations of the present invention. In effective amounts, such compounds cause tissue necrosis or shrinkage upon exposure. Any known ablation agent can be used according to the art, in concentrations as appropriate to the conditions while avoiding inactivation of the collagenase, with the amounts employed being readily determined by those of ordinary skill in the art. Typical concentration ranges are from about 1 to 95 wt % of ablation agent, more typically about 5 to 80 wt %. Ablation agents suitable for use with the invention include, but are not limited to osmotic-stress-generating agents (e.g., a salt, such as sodium chloride or potassium chloride), organic compounds (e.g., ethanol), basic agents (e.g., sodium hydroxide and potassium hydroxide), acidic agents (e.g., acetic acid and formic acid), enzymes (e.g., hyaluronidase, pronase, and papain), free-radical generating agents (e.g., hydrogen peroxide and potassium peroxide), oxidizing agents (e.g., sodium hypochlorite, hydrogen peroxide and potassium peroxide), tissue fixing agents (e.g., formaldehyde, acetaldehyde or glutaraldehyde), and/or coagulants (e.g., gengpin). These agents may be combined with collagenase in the same formulation so long as they do not negatively affect the enzymatic activity of the collagenase, or they may be administered separately, at the same time or at different times.

The methods according to the invention may be used in conjunction with any known treatments to control symptoms caused by fibroids. For example, NSAIDs or other analgesics can be used to reduce painful menses, oral contraceptive pills are may be prescribed to reduce uterine bleeding, and iron supplementation may be given to treat anemia. A levonorgestrel intrauterine device can be used to reduce hemorrhage and other symptoms if the condition of the uterus does not result in expulsion of the device.

The ability to non-invasively image regions where the formulations of the present invention are being introduced and where they have been introduced is a valuable diagnostic tool for the practice of the present invention. Therefore, in addition to a uterine fibroid treatment agent and any of the various optional components discussed above, the uterine fibroid formulations of the present invention also optionally include one or more imaging contrast agents to assist with guiding the clinician to administer the collagenase compound to the fibroid or tissue to be treated or to determine that administration has been correctly located. Non-noninvasive imaging techniques include magnetic resonance imaging (MRI), ultrasonic imaging, x-ray fluoroscopy, nuclear medicine, and others. Any contrast agent suitable for use with such techniques and known in the art can be used as part of the inventive compositions and formulations.

Any real-time imaging technology can be used to guide injection or insertion in the invention. For example, X-ray based fluoroscopy is a diagnostic imaging technique that allows real-time patient monitoring of motion within a patient. To be fluoroscopically visible, formulations are typically rendered more X-ray absorptive than the surrounding tissue. In various embodiments of the invention, this is accomplished by the use of contrast agents. Examples of contrast agents for use in connection with X-ray fluoroscopy include metals, metal salts and oxides (particularly bismuth salts and oxides), and iodinated compounds. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine.

Ultrasound and magnetic resonance imaging can provide two- and/or three-dimensional images of a portion of the body. Ultrasound and MRI are advantageous, inter alia, because they do not expose the patient or medical practitioner to harmful radiation and they can provide detailed images of the observed area. These detailed images are valuable diagnostic aids to medical practitioners and can be used to more precisely control the quantity and location of the formulations of the present invention.

Suitable ultrasonic imaging contrast agents for use in connection with the present invention include solid particles ranging from about 0.01 to 50 microns in largest dimension (e.g., the diameter, where spherical particles are used), more typically about 0.5 to 20 microns. Both inorganic and organic particles can be used. Examples include microparticles/microspheres of calcium carbonate, hydroxyapatite, silica, poly(lactic acid), and poly(glycolic acid). Microbubbles can also be used as ultrasonic imaging contrast agents, as is known in the imaging art. The ultrasonic imaging contrast agents for use in connection with the present invention are preferably biocompatible and stable in the formulation. Concentrations of the ultrasonic imaging contrast agents typically range from about 0.01 wt % to 10 wt % of the formulation, more typically about 0.05 to 2 wt %, where solid particles are used.

For contrast-enhanced MRI, a suitable contrast agent has a large magnetic moment, with a relatively long electronic relaxation time. Based upon these criteria, contrast agents such as Gd(III), Mn(II) and Fe(III) can be used. Gadolinium (III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) also are suitable. Further information can be found, for example, in U.S. Patent Application No. 2003-0100830 entitled "Implantable or insertable medical devices visible under magnetic resonance imaging," the disclosure of which is incorporated herein by reference.

The collagenase formulations described here preferably are injected into one or more individual uterine fibroid tumors using a hollow delivery channel, such as a hollow needle or cannula. For instance, administration can be performed using a needle in association with a conventional or specially designed syringe, cannula, catheter, and the like. A source of manual, mechanical, hydraulic, pneumatic or other means to apply pressure (e.g., a conventional syringe plunger, a pump, aerosol, etc.) can be used to inject the formulation into the fibroid. Alternatively, the formulations can be administered during surgery, for example via a trocar during laparoscopic surgery and during hysteroscopic treatment.

Injection routes include, for example, transabdominal, transcervical and transvaginal routes. Where the formulations have fluid attributes, the injection volume will vary, depending, for example, on the size of the fibroid, the type and concentration of treatment agent, and so forth, and will typically range from 1.0 to 10.0 ml per injection. Similarly, where formulations having solid attributes (e.g., pellets or powders) are used, the amount of formulation injected/inserted will also depend, for example, on the size of the fibroid, the type and concentration treatment agent utilized, etc. Multiple pellets or doses of collagenase composition can be administered at a single injection site. Regardless of the physical attributes of the formulation, multiple injection/insertion sites may be established within a single fibroid, with the number of injections depending on the size and shape of the fibroid as well as the type and/or concentration of the treatment agent that is used. Multiple fibroids or a single fibroid can be treated.

In various embodiments, the injection/insertion device is guided to the fibroid site under image guidance. Image guidance can include, for example, direct visual guidance (e.g., laparoscopic guidance in trans-abdominal procedures and hysteroscopic guidance in trans-vaginal procedures) and non-direct visual guidance (e.g., ultrasound guidance, fluoroscopic guidance, and/or MRI guidance).

As a specific example, visual guidance of the injection/insertion device is conducted laparoscopically using a scope that is positioned in the abdomen (e.g., by insertion through a trocar). In this way, a device (e.g., a delivery needle or canula) can be inserted percutaneously into the abdomen and guided under laparoscopic vision to the uterine fibroid. Once the fibroid is reached, fluoroscopy, MRI or ultrasound (e.g., trans-vaginal ultrasound, trans-abdominal ultrasound, intra-abdominal ultrasound, etc.) preferably is used to guide the tip of the delivery needle to a desired position within the fibroid, at which point the formulation is injected or inserted into the fibroid. To the extent that there is sufficient contrast between the formulation and the surrounding tissue, the location of the formulation within the fibroid will also be viewed.

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

EXAMPLES

Example 1. General Collagenase Production

To prepare an animal-material-free clostridia cell bank, *Clostridium histolyticum* cells are suspended in a medium containing a vegetable peptone and optionally yeast extract. For example, one general method for accomplishing this is as follows.

TABLE 2

General Method to Produce Clostridium Cell Bank.

| | |
|---|---|
| Step 1 | Starting cells: any *Clostridium histolyticum* culture which is convenient and available, for example *Clostridium histolyticum* ATCC 21000, strain 004 |
| Step 2 | Inoculate 1 mL of step 1 into 300 mL of media containing 15.45 g Phytone, 2.55 g yeast extract, and water sufficient to produce 0.3 L (M#1); |
| Step 3 | step 2 for 24 hours at 37° C. (1$^{st}$ culture); |
| Step 4 | Transfer 3 mL of step 3 (1$^{st}$ culture) to 1000 mL of M#1; |
| Step 5 | Incubate step 4 for 16 hours at 37° C. (2$^{nd}$ culture); |
| Step 6 | Centrifuge the 2$^{nd}$ culture; |
| Step 7 | Re-suspend the pellet with the 5 mL of media #1 and 5 mL of 20% glycerol; |
| Step 8 | Freeze the aliquot of cells gradually ; |
| Step 9 | Store the aliquot at −80° C. |

Once an animal material-free cell bank is established, the cells can be grown or fermented in convenient media known in the art, preferably non-animal-derived medium. The medium can optionally contain yeast extract. Exemplary, non-limiting examples of such media are M #1, M #2, M #3, and M #4 as described in Table 3, below. In addition, see Table 4 for an exemplary, non-limiting general example of the steps of the fermentation process.

TABLE 3

Media recipes and preparation.

| | M #1 | M #2 | M #3 | M #4 |
|---|---|---|---|---|
| Phytone | 15.45 g | | 103 g | |
| Veggitone | | 15.45 g | | 103 g |
| Yeast extract | 2.55 g | 2.55 g | 17 g | 17 g |
| KH$_2$PO$_4$ | | | 1.92 g | 1.92 g |
| K$_2$HPO$_4$ | | | 1.25 g | 1.25 g |
| Na$_2$HPO$_4$ | | | 3.5 g | 3.5 g |
| NaCl | | | 2.5 g | 2.5 g |
| vol of water | 0.3 L | 0.3 L | 1 L | 1 L |

TABLE 4

Fermentation Process.

| | |
|---|---|
| Step 1 | Starting cells: Animal material free clostridia cell bank |
| Step 2 | Inoculate 1 mL of step 1 into the 300 ml of M#1; |
| Step 3 | Incubate step 2 for 16 to 24 hours at 37° C. (1$^{st}$ culture); |

TABLE 4-continued

Fermentation Process.

| | |
|---|---|
| Step 4 | Transfer 10 mL of step 3 (1$^{st}$ culture) and 10 mL Vitamin/Mg solution* to 1000 mL of M#3, or 4 respectively; |
| Step 5 | Incubate step 4 for about 22 hours at 37° C. (2$^{nd}$ culture); |
| Step 6 | Use 2$^{nd}$ culture for downstream isolation and purification. |

*Prepared separately by dissolving 8 g MgSO$_4$, 1.2 g ferrous sulfate, 0.05 g riboflavin, 0.1 g Niacin, 0.1 g Calcium pantothenate, 0.1 g pimelic acid, 0.1 g pyridoxine, and 0.1 g thiamine in 1100 ml water, followed by sterilization by 0.22 um filtration.

After preparation of "2$^{nd}$ culture," the collagenase I and collagenase II can be isolated and purified using any method capable of producing each enzyme separately to at least 95% purity. The method may combine one or more of the steps of ammonium sulfate precipitation, dialysis, hydroxyapatite (HA) chromatography, gel filtration and ion-exchange, for example, preferably in that order. The gel filtration is preferably G75 gel filtration. The ion-exchange is preferably anion-exchange: Q-Sepharose chromatography. In addition, when the Clostridia have been cultured in medium containing less glucose and more salt compared to the majority of known bacterial culture, as preferred, protease inhibitors such as leupeptin are not required.

Example 2. Preparation of Animal Material Free *Clostridium* Cell Bank

The starter cell culture was *Clostridium histolyticum* ATCC 21000, strain 004 which was originally created with bovine-derived materials. The cells were first grown in animal material free medium (M #1, Table 3). Briefly, the recipe includes: phytone, 51.5 g, yeast extract 8.5 g, 1000 mL water. The pH was adjusted to 7.30 with NaOH, and the medium sterilized at 121° C. for 20 minutes. One milliliter of the starting material was then inoculated into 300 mL of M #1 and incubated for 24 hours at 37° C. (1st culture). Three milliliters of the 1st culture was transferred to 1000 mL of M #1 and incubated for 16 hours (2nd culture). The 2nd culture was then centrifuged aseptically. The pellet was re-suspended in 5 mL M #1 with 5 mL 20% glycerol. The aliquots of cell suspension were frozen gradually and stored at −80° C.

Example 3. Fermentation Process

*Clostridium histolyticum* ATCC 21000, strain 004 was inoculated into the starting culture with M #1 or M #2 and incubated at 37° C. for 16 hours. Ten milliliters of the starting culture (M #1 or M #2) and 10 mL Mg/vitamin solution (prepared separately by dissolving 8 g MgSO4, 1.2 g ferrous sulfate, 0.05 g riboflavin, 0.1 g Niacin, 0.1 g Calcium pantothenate, 0.1 g pimelic acid, 0.1 g pyridoxine, and 0.1 g thiamine in 1100 mL water, followed by sterilization by 0.22 μm filtration) was then transferred to each liter of M #3 or M #4 (or a variation thereof), and incubated for 22 hours. *Clostridium histolyticum* grew well with the OD600 reaching >2.5.

Example 4. General Procedure for Isolation and Purification of Collagenase I and Collagenase II

TABLE 5

General Exemplary, Non-Limiting Isolation and Purification Procedure for Collagenase I and Collagenase II.

| Stages of Product | Operations |
| --- | --- |
| Fermentation broth | Centrifugation or 1.0 µm filtration; |
| Clarified fermentation broth | Add ammonium sulfate (590 g/liter); centrifugation; |
| Crude collagenase precipitate | Dissolve crude collagenase precipitate by adding purified water; |
| Crude collagenase solution (store at −20° C.) | Dialyze crude collagenase solution against purified water overnight with 10 kDa pore size dialysis membrane; |
| Dialyzed crude collagenase | Clarify the dialyzed crude collagenase solution with either centrifugation or filtration or the combination of both; |
| Clarified solution | Add potassium phosphate buffer, pH 6.7 to a final conc. of 0.1M; |
| Collagenase in phosphate buffer | Load collagenase solution to hydroxylapatite column and elute column with gradient of increasing $K_2PO_4$ conc. at ambient temp. (20° C.); |
| Collagenase HA eluate | Concentrate the eluate with ultrafiltration (30 kDa of pore size); |
| Concentrated collagenase | Load the concentrate onto a G75 gel filtration column at ambient temperature (20° C.) and elute with 20 mM Tris/150 mM NaCl; |
| Collagenase G75 eluate | Dialyze the eluate against a buffer (10 mM Tris, 3 mM calcium chloride ($CaCl_2$), pH 8.0) overnight; |
| Dialyzed G75 eluate | Load dialyzed eluate on to a Q-Sepharose anion-exchange column at ambient temperature (20° C.); elute using a gradient of 10 mM Tris HCl, 3 mM $CaCl_2$, pH 8.0 buffer and 10 mM Tris HCl, 3 mM $CaCl_2$, 1M NaCl, pH 8.0 buffer; |
| Collagenase class I and class II fractions | Store separately at −20° C. |

Example 5. Ex Vivo Treatment of Uterine Fibroid Tissue

Figure 2:
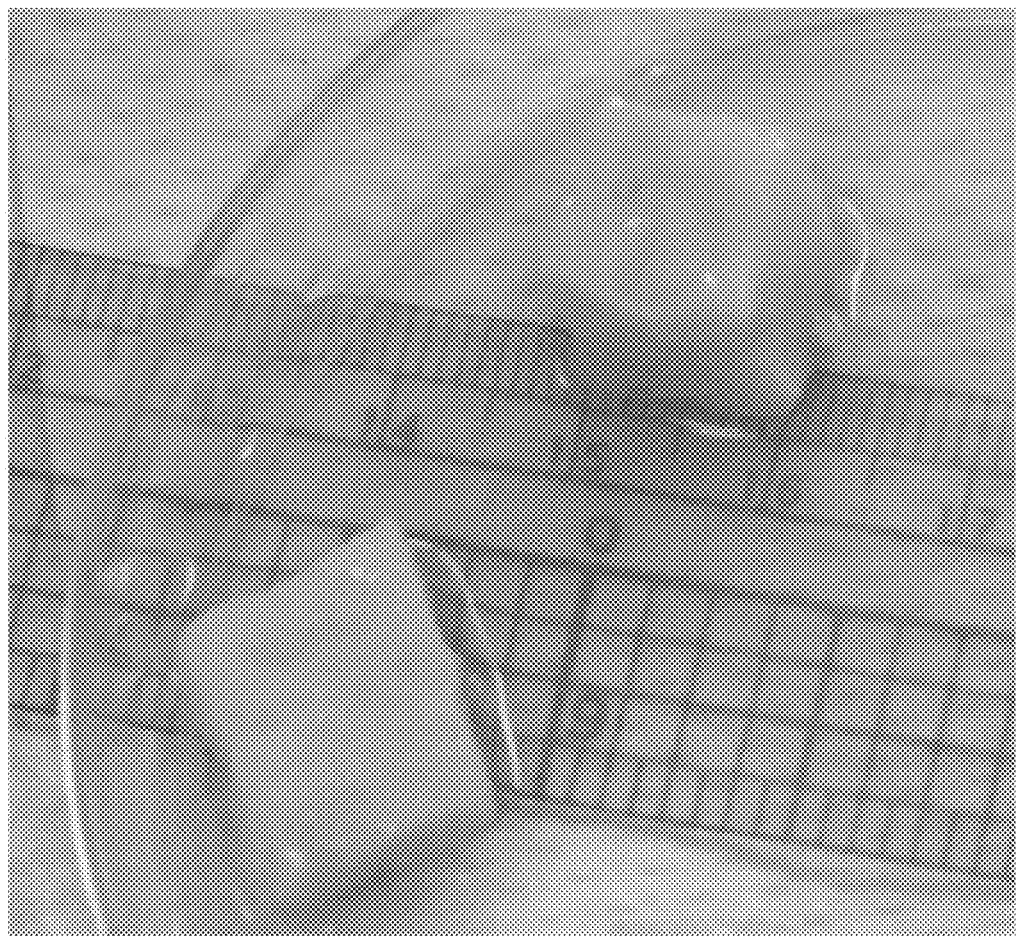
FIG. 2 is a photograph of uterine tissue cubes.
Figure 3A:
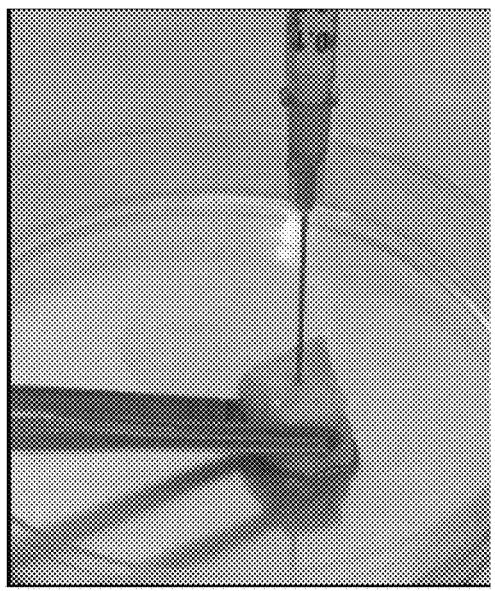
FIGS. 3A and 3B are photographs of a uterine tissue cube undergoing injection (FIG. 3A) and injected uterine tissue cubes undergoing incubation (FIG. 3B).
Figure 3B:
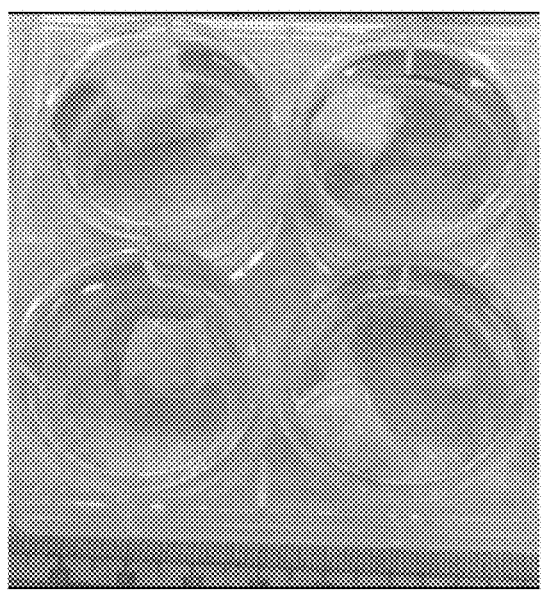

Samples of fibroid tissue and myometrium were obtained post-hysterectomy from women with consent and identified by evaluation by a surgical pathologist. The tissue samples were transported to the laboratory and cut into 1 $cm^3$ cubes. See FIG. 2. These cubes were injected with purified collagenase (0.06 or 0.2 mg in 100 µL) dissolved in media or serum and then incubated for 24, 48, 72, or 96 hours at 37° C. See FIG. 3. Each treatment was carried out in tissues from three different patients with two tissue samples per treatment because fibroid tissue is extremely variable. Control fibroid and myometrium cubes were injected with vehicle or sham injected. At the end of the incubation, the tissue samples were photographed to document gross appearance. Degree of liquefaction and softening was observed and documented using a 4-point subjective scale.

Samples were frozen for biomechanical assessment (compression analysis). Samples were fixed in formalin for histology and Masson trichrome and picrosirius red staining. They were analyzed by light microscopy for the presence or absence of collagen and assessed using computer morphometry to determine the extent of degradation. In the case of picrosirius red staining, polarized light microscopy was performed to determine collagen fiber orientation. Samples were fixed in glutaraldehyde and postfixed with osmium tetraoxide for electron microscopy to determine collagen fibril orientation and evidence of fibril degradation. Additional injections were done at a dose of 0.58 mg/injection (250 ul of 2.3 mg/ml).

These ex-vivo studies have shown the efficacy of purified collagenase in softening and partial liquefaction of post-hysterectomy fibroid specimens, as well as a decrease in the collagen content. Treated fibroid-specimens were grossly softer and had partially liquefied centers. Masson trichrome and picrosirius red stains of theses tissues showed a dramatic subjective decrease in collagen content compared to fibroid tissue injected with vehicle.

Example 6. Treatment of Whole Uterine Fibroids Ex Vivo

Donated tissue was obtained from four female adult patients 18 years of age or older who can give legally effective consent and who were planning to undergo definitive treatment for fibroids by hysterectomy. After the removal of the hysterectomy specimen, the uterus was observed grossly by standard procedures by a surgical pathologist. Complete fibroids (submucosal (abutting the endometrium), intramural (within the myometrium), and subserosal (abutting the uterine serosa) fibroids, or pedunculated fibroids (attached to the uterus by a stalk) if they are present) from 1 to 4 cm (including the capsule) along with 1.5 cm of the surrounding adjacent myometrium and, if available, a 0.5 cm section of endometrium were dissected free from the specimen and placed in normal saline.

Tissues were brought to the laboratory immediately, washed and injected with purified *Clostridium histolyticum* collagenase (PCHC) (0.1 mg/100 µl/$cm^3$). Optionally, a higher concentration of the collagenase was used to decrease the volume of the injection. Purified collagenase was diluted in 0.3 mg/mL calcium chloride dihydrate in 0.9% sodium chloride, optionally combined with 1% methylene blue as a marker to visually assess the area of distribution of the injected material within the fibroid and uterus. Fibroids were injected with PCHC or vehicle in the center of the obtained specimen. See FIGS. 4A and 4B. The amount of collagenase injected depended on the size of the fibroids (1-4 cm). Generally, about 818 µL of material was injected into a fibroid with a diameter of about 2.5 cm. If injecting the entire treatment volume centrally was not feasible due to tissue resistance to the injection or other factors, multiple locations were injected within the fibroid. The fibroid tissue then was incubated in DMEM/F12 culture medium at 37° C. for 24 hours. At least one fibroid with attached myometrium served as the control. This specimen received an injection of 1% methylene blue in vehicle without collagenase as a non-randomized placebo injection, centrally into the fibroid.

Color photographs were taken of the uterus and of the fibroid and myometrial pieces pre- and post-injection. Fibroid diameters were measured with a metric ruler.

At the end of the incubation, the samples were reassessed grossly for size, consistency and firmness, and color photographs were obtained, as well as optional video recording to record fibroid manual distensibility and any liquefied portions upon sectioning. The degree of liquefaction and softening were observed and documented using a 4-point subjective scale.

Whether the collagenase can penetrate the capsule and affect the nearby myometrium was determined. Samples were obtained, including tissue from the injected fibroid and adjacent tissue, plus a section that included fibroid and adjacent myometrium and/or endometrium still attached, and myometrium alone. Samples were fixed in formalin for histology and Masson trichrome, picrosirius red, and hematoxylin-eosin staining. The samples were analyzed by light microscopy for the presence or absence of collagen and using computer morphometry to assess the extent of degradation. Picrosirius red staining was used with polarized light microscopy to determine collagen fiber orientation.

Figure 5:
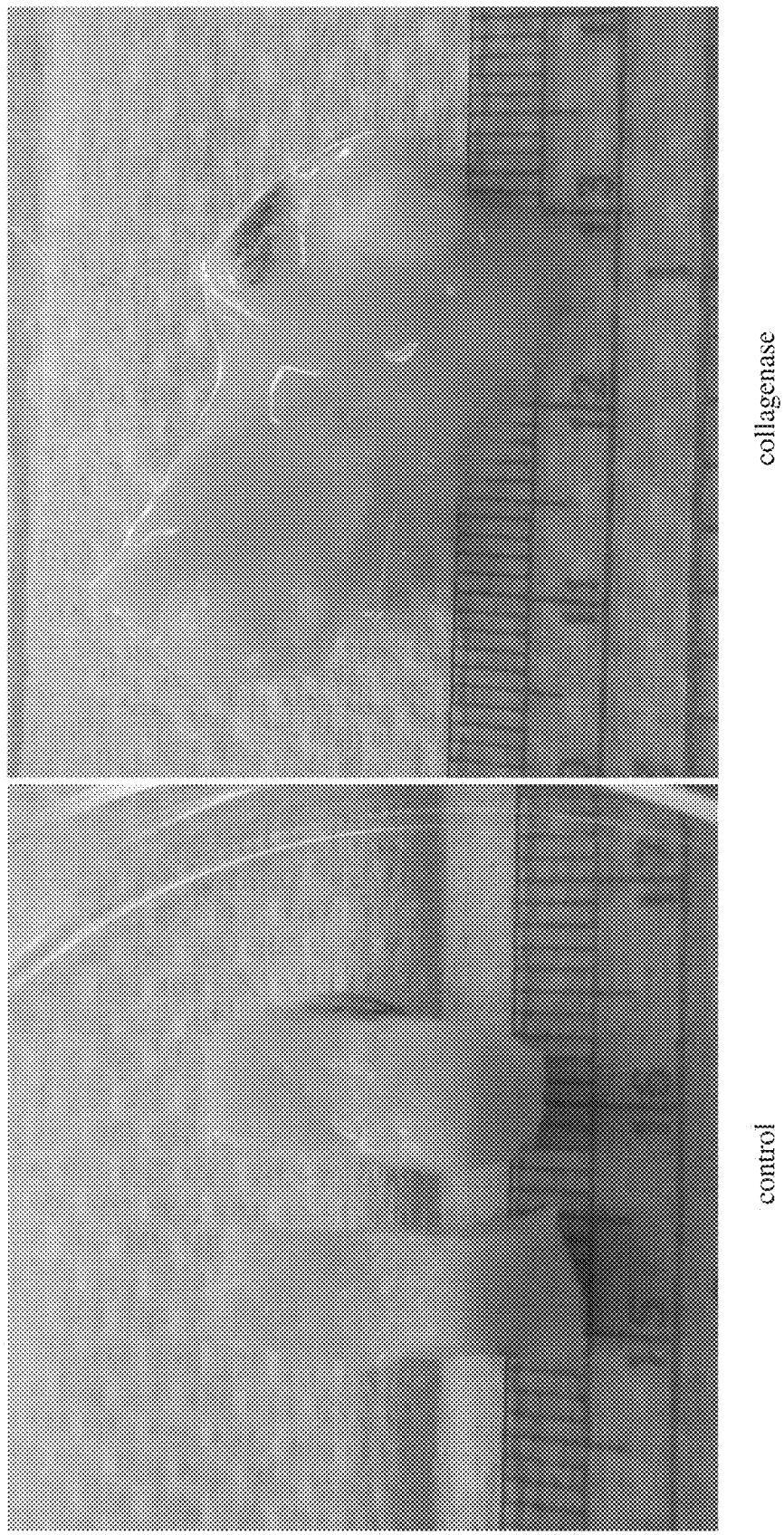
FIG. 5 is a pair of photographs showing fibroid tissue cubes injected with vehicle (control) or collagenase, after 48 hour incubation.

Exemplary treatment schemes for each patient:
fibroid 1: inject 818 µL 1 mg/mL collagenase;
fibroid 2: inject 818 µL 1 mg/mL collagenase;
fibroid 3: inject 818 µL control vehicle;

Injections were given through the fibroid capsule into the center of the fibroid, through the myometrium into the center of the fibroid, or through the endometrium into the center of the fibroid, simulating in vivo injection routes. The fibroids here were liquefied in the same manner as shown in FIG. 5 (see below).

Example 7. Biomechanical Evaluation of Human Uterine Fibroids after Injection with Purified Clostridial Collagenase The two collagenases isolated from *Clostridium histolyticum* (ABC I and ABC II) were combined in a 1:1 mass ratio. Both collagenases are metalloproteases and have a broad hydrolyzing reactivity and degrade type I and III collagens. The biomechanical properties of uterine fibroid tissue were analyzed by rheometry in control and collagenase-treated specimens.

Uterine fibroids have been shown to contain about 70% Type I collagen compared to about 80% in myometrium; about 28% Type III collagen compared to about 20% in myometrium; and about 5% Type V collagen compared to about 2% in myometrium. Type I/III is lower at the center and the edge of fibroids as compared to myometrium. (Feng et al, Fibroid tissue was obtained after surgery (hysterectomy or myomectomy) from 4 different patients and cut into cubes (1 $cm^3$; n=43). Tissue cubes were injected into the center with 100 µL of purified collagenase (0, 0.25, 0.5, 1.0, 2.0 mg/mL; n=4-14 per dose) and incubated at 37° C. for 24, 48, or 96 hours. At the end of the incubation period, cubes were cut in half and snap-frozen in liquid nitrogen. Different degrees of softening and liquefaction at the center were noted. An AR-G2 rheometer was used to measure the sample stiffness dynamically (complex shear modulus (Pa) at 10 rad/sec), taking into account both the viscous and elastic behavior of the material. At least 2 specimens (5 mm diameter punch) from each tissue cube were measured. Data were analyzed by 2-way ANOVA and Dunnett's multiple comparisons test.

Overall, stiffness in control fibroid cubes (6585±707 Pa; n=13) was greater than in treated cubes (2003±275 Pa; n=30; p<0.0001). More specifically, stiffness in fibroid tissues was reduced in a time and dose dependent manner. At 48 hours, treatment with 0.25 mg/mL did not reduce stiffness (5032±1796 Pa), but treatment with 0.5 mg/mL did (2014±1331 Pa; p 0.05). At 96 hours, both the 0.25 and the 0.5 doses were effective (1720±377 and 1072±160 Pa; p 0.01). The 1.0 and 2.0 mg/mL treatments reduced stiffness at 24 hours, but not significantly (2177±37 and 2480±984 Pa; n=4). However, doses of 1.0 and 2.0 mg/mL were effective at 48 hours (3588±637; p 0.05 and 1254±445 Pa; p 0.01; n=6) and at 96 hours (921±305 and 1350±571 Pa; p 0.0001; n=10).

Using a torsional rheometer, tissue stiffness was quantitated over a wide range (very firm to liquefied). Our data indicate that treatment of the fibroid tissue with defined doses of purified clostridial collagenase significantly decreased the stiffness (modulus) of the tissue. See FIG. 5, which shows collagenolysis in fibroid tissue after 48 hour incubation. The left photograph is tissue that was injected with vehicle (control) and the right photograph is tissue that was injected with collagenase. FIG. 6 shows micrographs of control (FIGS. 6A and 6B) and collagenase-treated (FIGS. 6C and 6D) tissue. Mason stain in Figures A and C (left) shows that collagen is decreased. Picrosirius red stain visualized under polarized light (FIG. 6D) clearly shows in the bottom right that collagen fibers are degraded.

Example 8. Treatment of Human Uterine Fibroids in Nude Mouse Model

The xenograft mouse model, in which three-dimensional organotypic cultures of human uterine fibroid cells are implanted under the skin of female nude mice, has been successfully employed to study keloids, a fibrotic skin disorder with biology similar to fibroids. This model is used to demonstrate effects of PCHC injection, in an HPG nanocarrier formulation, on fibroid tissue in vivo.

Polylactic acid sponges, other synthetic polylactic acid scaffolds, or any suitable commercially available scaffold is inoculated with human uterine fibroid cells to produce an organotypic 3-D culture of uterine fibroid cells that can be implanted into nude mice. These 3-dimensional organotypic cultures (3D-fibroids) are representative of human fibroids and produce and contain extracellular matrix.

Figure 7:
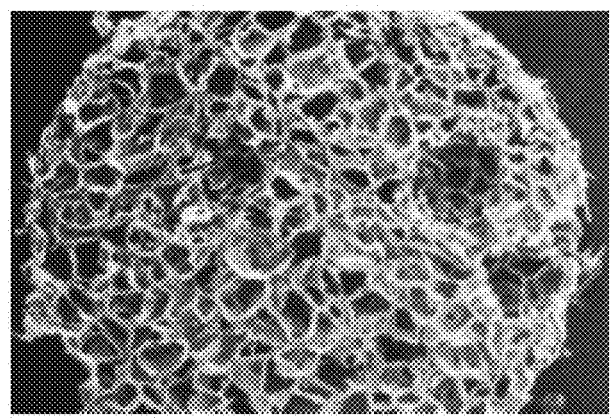
FIG. 7 is a scanning electron micrograph of the BD 3D OPLA® scaffold.

OPLA sponges (Open-Cell Polylactic Acid, BD Biosciences; FIG. 7) are synthetic polymer scaffolds that are synthesized from D,D-L,L polylactic acid. This material has a facetted architecture which is effective for culturing high density cell suspensions. The cells will be seeded onto the 3D sponge-like scaffolds under dynamic conditions, leading to uniform cell population throughout the sponges and higher cell numbers per sponge than static seeding. Post-sterilization, the molecular weight of the OPLA is 100-135 kD. They have an approximate size of 5 mm×3 mm (0.04 $cm^3$) with an average pore size of 100-200 µm.

Cells and scaffolds are placed into cell culture chambers of a bioreactor consisting of a fluid (culture media)-filled, rotating chamber that allows for constant floating of cells while minimizing shearing forces and gravitational settlement of cells and/or scaffolds (Synthecon, Inc.). Cells inside the rotating bioreactor chamber are suspended in virtual weightlessness.

Figure 8:
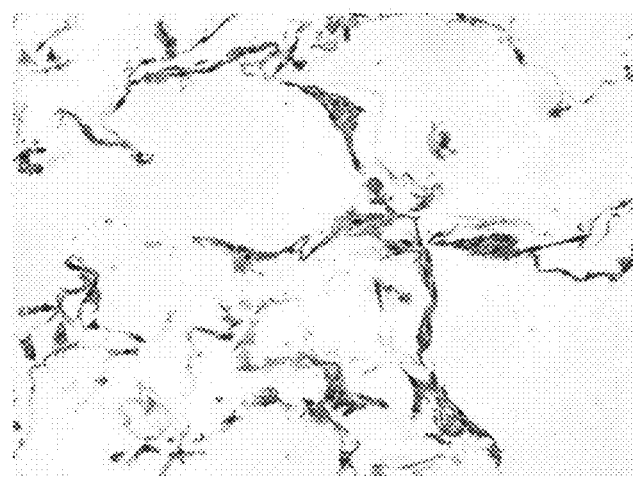
FIG. 8 is a micrograph showing H&E stain of fibroid cells seeded onto an OPLA scaffold and cultured for 9 days (Zeiss Axio Imager® widefield fluorescence microscopy).

Primary human fibroid cells from specimens obtained at hysterectomy are seeded statically or dynamically into OPLA sponges and grown for 30 days to allow for production and assembly of extracellular matrix. Cells grow throughout the scaffold and can be formalin fixed, paraffin embedded and thin sectioned for observation, optionally with staining for multiple markers. See FIG. 8, which shows the formation of the cell lattice following the outlines of the sponge-like scaffold.

Figure 9A:
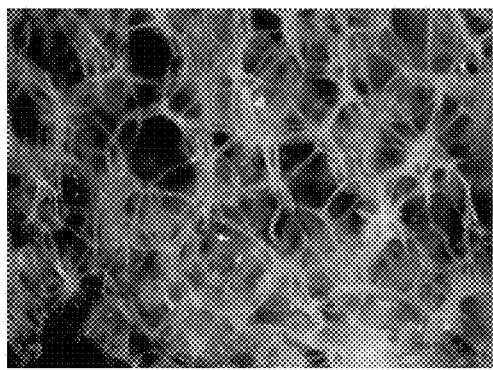
FIG. 9A is a bright field image and FIG. 9B is a bright field image with fluorescent image overlay showing primary cultures of fibroid cells 8 days after static seeding (Zeiss Lumar® stereoscopic image, stained with fluorescein-phalloidin for f-Actin).
Figure 9B:
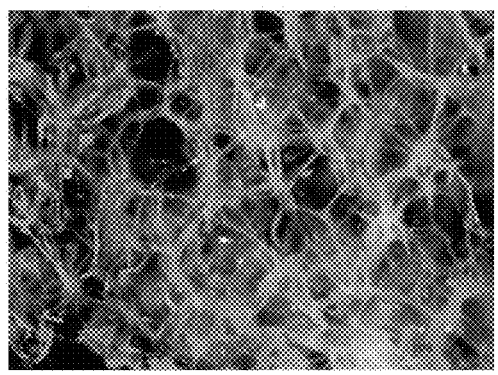
Figure 10A:
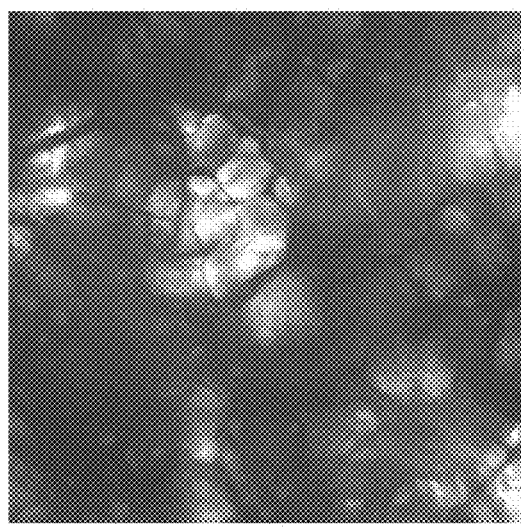
FIGS. 10A and 10B are micrographs showing primary fibroid cells cultured on OPLA scaffolds and fixed in situ taken from the same field of vision every 10 micrometers.
Figure 10B:
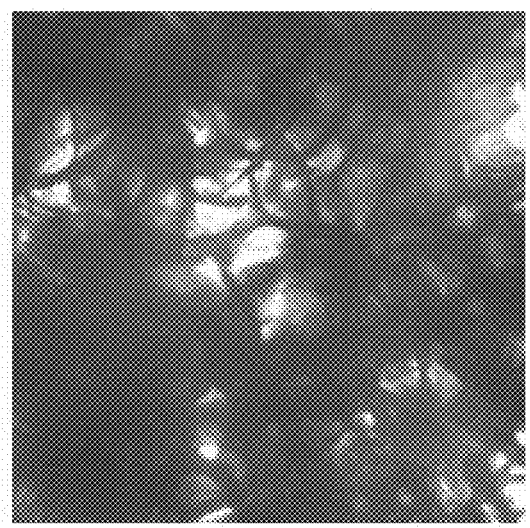
Figure 11:
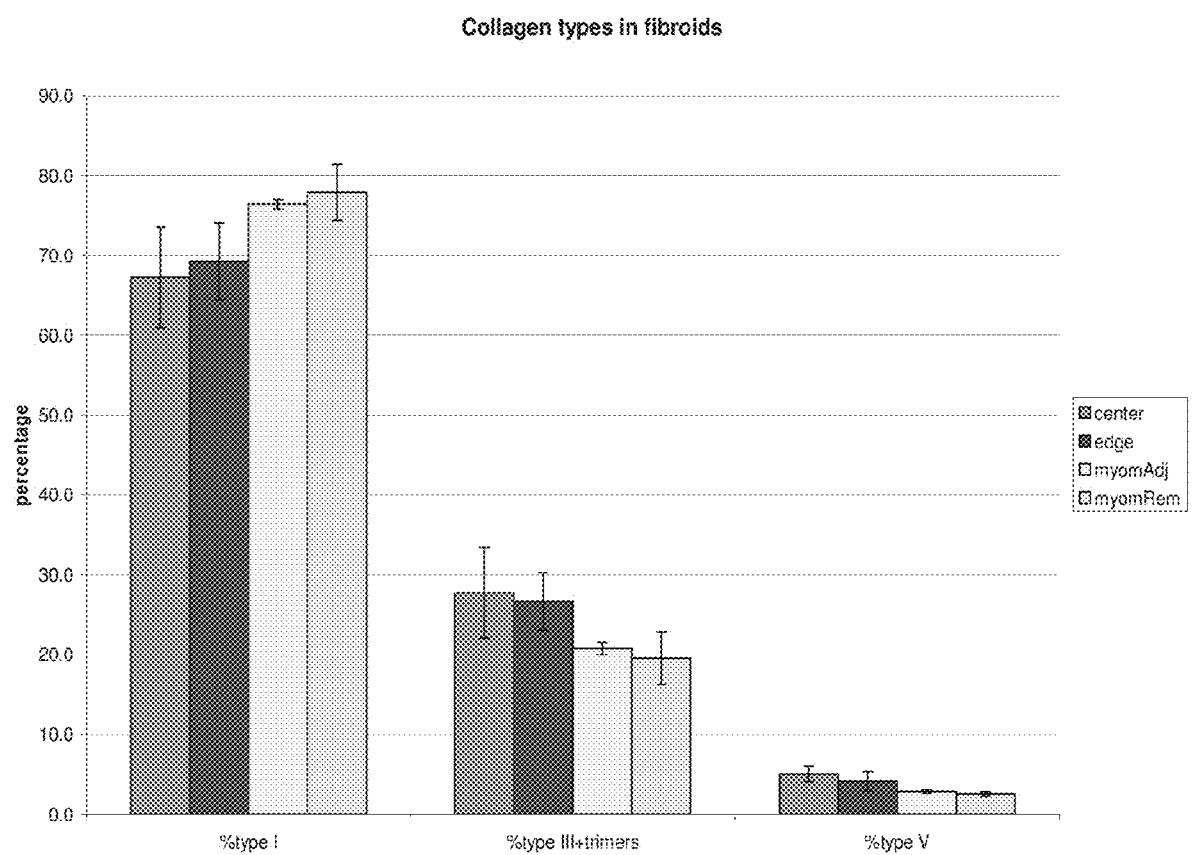
FIG. 11 is a bar graph showing the percentages of the types of collagen in fibroids.
Figure 12:
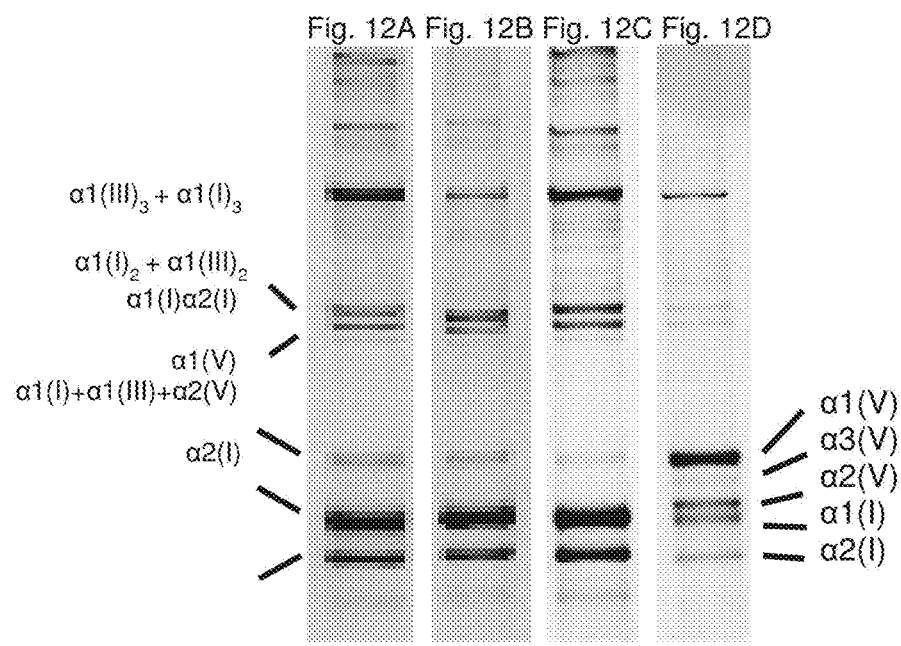
FIGS. 12A-12D show SDS-PAGE analysis of collagen content in a fibroid sample (Nydea Aviles and Sergey Leikin, NIH).
Figure 13:
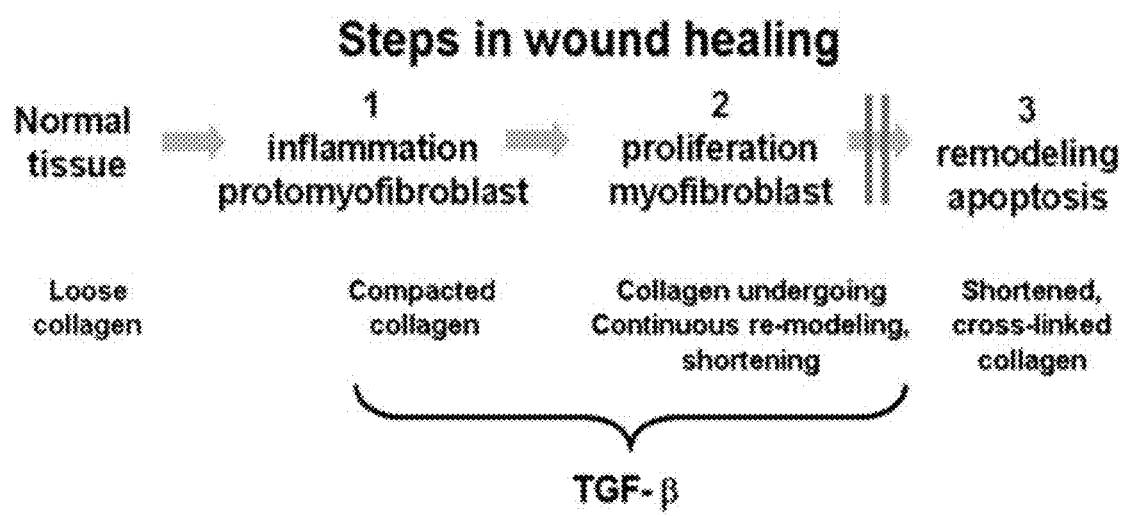
FIG. 13 shows how TGF-β may be involved in fibrosis, which may be considered a form of altered tissue repair. Cell injury in myometrial cells leads to activation of repair. In fibroids, wound healing halts at the proliferation stage, collagen accumulates. (Leppert et al. A new hypothesis about the origin of uterine fibroids based on gene expression profiling with microarrays. *Am J Obstet Gyn* 2006; 95: 415-20.)
Figure 14A:
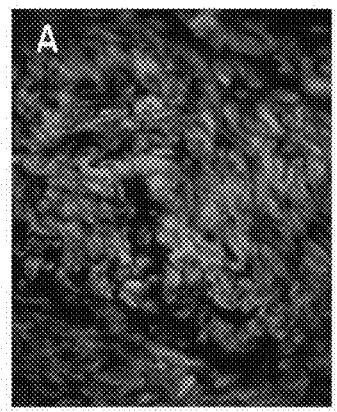
FIGS. 14A-14D show structural changes associated with uterine fibroids. The change in cell shape from smooth muscle to fibroid cell appears to be a myofibroblast-like cell, suggesting that mechanotransduction plays a role in fibroid formation.
Figure 14B:
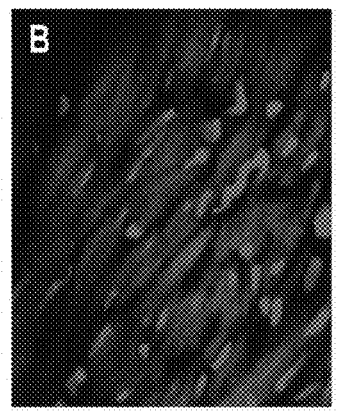
Figure 14C:
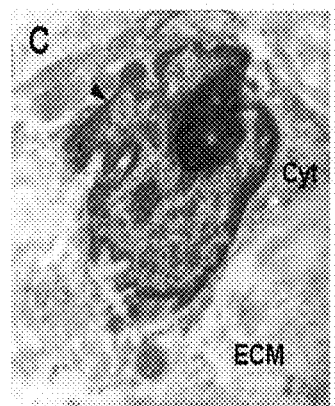
Figure 14D:
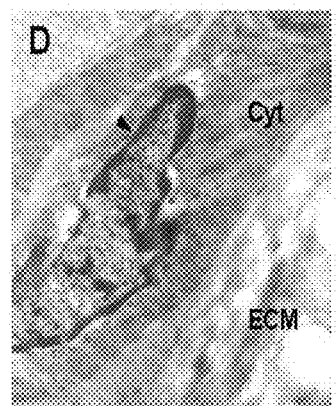

FIG. 9 shows primary cultures of fibroid cells after static seeding. The cells are fixed on the scaffold and observed in situ. Scaffolds containing cells were fixed and were unstained (FIG. 9A) or stained for f-actin with fluorescent phalloidin (FIG. 9B). Cells were evenly distributed throughout the scaffold. The imaged scaffolds are >1 mm thick and therefore not all cells are in focus, indicating that the cells are growing not only on the surface, but also deep inside the scaffolds. FIG. 10 shows the population of cells throughout the sponge-like scaffolds using confocal microscopy (FIGS. 10A and 10B).

High quality RNA is extracted from the 3D-cultures of fibroid cells on OPLA sponges and used to verify the expression of two genes of interest. Versican and TGFβ3 are known to be highly expressed in fibroid tissue and cells. Results in Table 6 show that both a fibroid cell line and primary cultures of fibroid cells in this 3D-culture system express these two genes in high amounts.

TABLE 6

Real Time PCR Assay Results

| | CDNA (ng) per reaction | Threshold Cycle Ct (mean ± SEM) | |
|---|---|---|---|
| | | Versican | TGFβ$_3$ |
| Fibroid Cell Line | 50 | 22.1 ± 0.07 | 26.8 ± 0.07 |
| Primary Fibroid Cells | 25 | 22.2 ± 0.21 | 24.0 ± 0.04 |

The patent and scientific literature referred to herein establishes the knowledge that is available to those with skill in the art. All United States patents and published or unpublished United States patent applications cited herein are incorporated by reference in their entireties for all purposes. All published foreign patents and patent applications cited herein are hereby incorporated by reference in their entireties for all purposes. All other published references, documents, manuscripts and scientific literature cited herein are hereby incorporated by reference in their entireties for all purposes.

While this invention has been particularly shown and described with references to preferred embodiments thereof, it will be understood by those skilled in the art that various changes in form and details may be made therein without departing from the scope of the invention encompassed by the appended claims.

REFERENCES

Abedin et al., Biochem Biophys Res Commun 1981; 102(4): 1237-1245.
Aitken et al., Hum. Reprod. 2006; 21(10): 2669-2678.
Arici et al., Fertil Steril 2000; 73(5): 1006-1011.
Arslan et al., Hum Reprod 2005; 20(4): 852-863.
Aviles et al., Advances in Uterine Leiomyoma Research: 3rd NIH International Congress, 2010.
Bae et al., Pharm Res 1991; 8(4): 531-537.
Barrett J C. Molecular Characterization of Uterine Leiomyoma. In: Presented at: Advances in Leiomyoma Research: 2nd NIH Intl Congress. Bethesda, Md.; 2005.
Behera et al., Hydroxyproline. Reprod Sci 2007; 14(8 Suppl): 63-76
Bolgen et al., Biomater Sci Polym Ed 2007; 18(9): 1165-1179.
Breech et al., "Leiomyomata uteri and myomectomy". In: TeLinde's Operative Gynecology, 9th ed. Philadelphia: Lippincott, Williams and Wilkins; 2003: 753-799.
Catherino W H, "Annual Meeting of the American Society for Reproductive Medicine." 42nd Annual Postgraduate Program 2009: P 35.
Catherino et al., Genes, Chromosomes and Cancer 40(3): 204-217, 2004.
Chen et al., J Clin Endocrinol Metab. 2006 April; 91(4): 1296-304.
Chung et al., J Biol Chem 2008; 283(38): 25879-25886.
Chwalisz et al., Endocrine Reviews 2005; 26(3): 423-438.
Chwalisz et al., Fertility & Sterility 2007; 87(6): 1399-1412.
Das et al., Endocrinology 1992; 130(6): 3459-3466.
Feng et al., Thrombospondin-1 in an early uterine fibroid development model. American Society for Matrix Biology Biennial Meeting 2008; Abstract #168.
Feng et al., Reproductive Sciences 17, 3; 711, 2010.
Frey and Haag, Rev. Mol. Biotechnol. 2002; 90: 257-267.
Geever et al., Eur Polym J 2006 42(1): 69-80.
Graham et al., Nucleic Acid Res 1993; 21(16): 3737-3743.
Hatefi et al., Journal of controlled Release 2002 80(1-3): 9-28.
Hennessy et al., Lancet Oncol 2004; 5(6): 341-353.
Heskins M, Guillet J E; J Macromol Sci. Part A—Chem 1968; 2(8): 1441-1455.
Huang et al., Macromolecules 2008; 41(22): 8339-8345.
Ibraheem et al., Towards water-soluble star copolymer-drug conjugates. Proc. of 58th Conf. of South East Regional Amer. Chem. Society, Nov. 1-4, 2006, Augusta GA.
Jemal et al., Cancer statistics, 2005. CA Cancer J Clin 2005; 55(1): 10-30.
Jenison et al., Antisense & Nucleic Acid Drug Dev., 1998; 8(4): 265-279.
Joffe et al., Mod Pathol 2009; 22(3): 450-459.
Joseph et al., Fertil Steril 2010; 93(5):1500-8.
Kainthan et al., Macromolecules 2006; 39(22): 7708-7717.
Kao et al., Connect Tissue Res 1977; 5(2): 127-129.
Kohori et al., Journal of Controlled Release 1998; 55(1): 87-98.
Kose O, Waseem A., Dermatol Surg 2008; 34(3): 336-346.
Kuroda et al., J Invest Dermatol 1999; 112(5): 706-710.
Le Ray et al., J. Pharm. Sci. 1994; 83(6): 845-851.
Lee B H, Vernon B, Macromol Biosci 2005; 5(7): 629-635.
Lee B S, Nowak R A., J Clin Endocrinol Metab 2001; 86(2): 913-920.
Leppert et al., Fertil Steril 2004; 82 Suppl 3: 1182-1187.
Leppert et al., American Journal of Obstetrics and Gynecology 195(6): 415-420, 2006
Malik M, Catherino W H., Fertil Steril 2007; 87(5): 1166-1172.
Matchar et al., Evid Rep Technol Assess (Summ) 2001 (34): 1-6.
Mitsiades et al., Cancer Cell 2004; 6(5): 439-444.
Moulin et al., J Cell Physiol 2004; 198(3): 350-358.
Naitoh et al., Genes Cells 2005; 10(11): 1081-1091.
Norian et al., Matrix Biol. 2012; 31(1); 57-65.
Norian et al., Reproductive Sciences 2007; 14: 79A.
Norian et al., Reprod Sci 2009 16(12): 1153-1164.
Oudshoorn et al., Biomaterials 2006; 27(32): 5471-5479.
Peddada et al., Proc Natl Acad Sci USA 2008; 105(50): 19887-19892.
Pfaffl M W. Nucleic Acids Res 2001; 29(9): e45.
Rogers et al., Am. J. Obstet. Gynecol. 2008; 198(4): 474.e1-11.
Sasaki et al., J Clin Endocrinol Metab 2007; 92(2): 616-623.
Schmittgen T D, Zakrajsek B A. J Biochem Biophys Methods 2000; 46(1-2): 69-81.
Sosic et al., J Gynaecol Obstet 1996; 54: 245-250.
Sunder et al., Macromolecules 1999; 32(13): 4240-4246.
Takamoto et al., Connect Tissue Res 1998; 37(3-4): 163-175.
Taylor D K, "The Hyperbranched Polyglycerol Platform: Approaching the ideal-drug delivery system." Proceedings of Abstracts for Duke University Research Day May 6, 2009, Duke University.
Trueb B, Bornstein P, J Biol Chem 1984; 259(13): 8597-8604.

Walocha et al., Hum Reprod 2003; 18(5): 1088-1093.
Wang et al., Hum Reprod 2006; 21(7): 1869-1877.
Wei et al., Fertil Steril 2006, 85(1): 179-187.
Weston et al., Mol Hum Reprod 2003; 9(9): 541-549.
Wu et al., Cochrane Database Syst Rev. 2007: CD005287.
Wu et al., Matrix Biol 2005; 24(1): 3-13.
Xu et al., J Clin Endocrinol Metab 2005; 90: 953-961.
Yu et al., Proc Soc Exp Biol Med 1995; 209: 360-368.
Zhao et al., Mol Hum Reprod 2007; 13: 343-349.

The invention claimed is:

1. A method for the treatment of a uterine fibroid in a patient, comprising administering into the uterine fibroid a composition comprising from 0.25 mg/mL to 2.0 mg/mL of collagenase comprising collagenase I and collagenase II from *Clostridium histolyticum*, wherein the administering results in an at least 20% reduction in the stiffness of the uterine fibroid, as determined by the complex shear modulus (Pa) of the uterine fibroid at 96 hours following the administering.

2. The method of claim 1, wherein the composition is delivered through a delivery channel into the fibroid, wherein the delivery channel is in a needle, syringe, cannula, catheter, or jet injector.

3. The method of claim 1, wherein the composition comprises 0.25 mg/mL of collagenase from *Clostridium histolyticum*.

4. The method of claim 1, wherein the composition comprises 0.5 mg/mL of collagenase from *Clostridium histolyticum*.

5. The method of claim 1, wherein the composition comprises 1.0 mg/mL of collagenase from *Clostridium histolyticum*.

6. The method of claim 1, wherein the composition comprises 2.0 mg/mL of collagenase from *Clostridium histolyticum*.

7. The method of claim 1, wherein the composition is injected or inserted into the fibroid under image guidance, wherein the image is a scope image, an MRI image, an ultrasound image, or a fluoroscopic image.

8. The method of claim 1, wherein the composition further comprises a chemical ablation agent, a non-steroidal anti-inflammatory drug, an oral contraceptive, a gonadotrophin-releasing hormone (GnRH) agonist, an antiprogestogen, or a selective progesterone receptor modulator.

9. The method of claim 1, wherein the composition is a solid dosage form having a largest dimension between 1 mm and 20 mm.

10. The method of claim 1, wherein the composition further comprises a viscosity adjusting agent which is present in an amount effective to provide a viscosity ranging from 10,000 centipoise to 50,000 centipoise.

11. The method of claim 1, wherein the composition provides sustained release of an amount of the collagenase sufficient to treat the uterine fibroids.

* * * * *